(12) United States Patent
Rosen

(10) Patent No.: US 9,682,048 B1
(45) Date of Patent: Jun. 20, 2017

(54) MULTI-COMPONENT FORMULATIONS FOR THE TREATMENT OF COGNITIVE DECLINE INCLUDING ALZHEIMER'S DISEASE

(71) Applicant: Gene S. Rosen, Miami, FL (US)

(72) Inventor: Gene S. Rosen, Miami, FL (US)

( * ) Notice: Subject to any disclaimer, the term of this patent is extended or adjusted under 35 U.S.C. 154(b) by 532 days.

(21) Appl. No.: 13/912,844

(22) Filed: Jun. 7, 2013

Related U.S. Application Data

(63) Continuation-in-part of application No. 13/271,266, filed on Oct. 12, 2011, now abandoned.

(60) Provisional application No. 61/852,511, filed on Mar. 18, 2013, provisional application No. 61/404,769, filed on Oct. 12, 2010.

(51) Int. Cl.
| | | |
|---|---|---|
| *A61K 36/00* | (2006.01) | |
| *A61K 31/10* | (2006.01) | |
| *A61K 31/05* | (2006.01) | |
| *A61K 31/12* | (2006.01) | |
| *A61K 31/202* | (2006.01) | |
| *A61K 31/7024* | (2006.01) | |
| *A61K 36/45* | (2006.01) | |

(52) U.S. Cl.
CPC .............. *A61K 31/10* (2013.01); *A61K 31/05* (2013.01); *A61K 31/12* (2013.01); *A61K 31/202* (2013.01); *A61K 31/7024* (2013.01); *A61K 36/45* (2013.01)

(58) Field of Classification Search
None
See application file for complete search history.

(56) References Cited

U.S. PATENT DOCUMENTS

| | | | |
|---|---|---|---|
| 5,516,526 A | 5/1996 | Da La Torre | |
| 7,151,088 B2 | 12/2006 | Moessler et al. | |
| 2004/0241256 A1* | 12/2004 | Ehrenpreis | A61K 31/737 424/734 |
| 2006/0216251 A1 | 9/2006 | Morariu | |
| 2007/0269454 A1 | 11/2007 | Maeda et al. | |
| 2008/0213401 A1* | 9/2008 | Smith | A23L 1/30 424/657 |
| 2009/0312273 A1* | 12/2009 | De La Torre | A61K 31/10 514/23 |
| 2009/0326275 A1 | 12/2009 | DiMauro | |
| 2012/0263698 A1* | 10/2012 | Barber | A61K 31/05 424/94.1 |

FOREIGN PATENT DOCUMENTS

| | | | |
|---|---|---|---|
| RU | 2478376 C1 * | 4/2013 | |
| WO | WO 2007/033082 A2 | 3/2007 | |
| WO | WO 2011/123695 A1 | 10/2011 | |
| WO | WO 2012/159092 A2 * | 11/2012 | |

OTHER PUBLICATIONS

Lee et al: Perspectives on the Amyloid-B Cascade Hypothesis. Journal of Alzheimer's Disease 6 (2004) 137-145.
Whitehouse et al: Is Alzheimer's Disease an Outmoded Concept?—Putting the Patient and the Science First. International Conference on Alzheimer's Disease 2008. Poster P1-383. (Abstract Only).
Mawuenyega et al: Decreased Clearance of CNS β-Amyloid in Alzheimer's Disease. Science Dec. 2010: 330:177.4.
Venkataraman et al: Essential or Toxic? The Two Faces of the Abeta42 Peptide. International Conference on Alzheimer's Disease 2008. Poster P4-233. (Abstract Only).
Luchsinger et al: Relation of Diabetes to Mild Cognitive Impairment. International Conference on Alzheimer's Disease 2006. Poster P3-129.
Cooper: Biotin Deficiency and Sodium-Dependent Multi-Vitamin Transporter Dysregulation Triggers the Alzheimer's Cascade. International Conference on Alzheimer's Disease 2008: Abstract and Poster P4-418.
Tucker et al: High Homocysteine and Low B Vitamins Predict Cognitive Decline in Aging Men: the Veterans Affairs Normative Aging Study. American Journal of Clinical Nutrition Sep. 2005; 82(3), 627-635. (Abstract Only).
De Lau et al: Folate Levels and Cognitive Performance. International Conference on Alzheimer's Disease 2006 Poster P1-205.
Clarke et al: Vitamin B-12, Holotranscobalamin and Risk of Cognitive Decline: 10-Year Follow-Up of the Oxford healthy Aging Project. International Conference on Alzheimer's Disease 2006 Poster P3-126.
Morris et al: Dietary Copper and High Saturated and trans Fat Intakes Associated with Cognitive Decline. Archives of Neurology Aug. 2006; 63:1083-1088. (Abstract Only).
Bates et al: Relationship between Cardiovascular Disease Risk Factors and Alzheimer's Disease Aβ Protein in Subjective Memory Complainers. International Conference on Alzheimer's Disease 2008 Poster P1-342. (Abstract Only).
Qiu et al: Is Low Blood Pressure a Risk Factor for Dementia and Alzheimer's Disease in the Elderly? International Conference on Alzheimer's Disease 2006 Poster P1-232.
Caprini et al: Mental Activity and Dementia Risk. International Conference on Alzheimer's Disease 2006 Poster P4-170.
Gao et al: Selenium and Cognitive Function in Rural Elderly Chinese. International Conference on Alzheimer's Disease 2006 Poster P3-124.
Kaufman et al: Cognitive Decline in Alzheimer's disease: Impact of Spirituality, Religiosity and QOL. Neurology May 2007; 68 (18):1509-1514. (Abstract Only).

(Continued)

*Primary Examiner* — Qiuwen Mi
(74) *Attorney, Agent, or Firm* — Thrive IP®; Jeremy M. Stipkala

(57) ABSTRACT

A multi-component formulation for the treatment, delay, and/or prevention of cognitive decline, including Alzheimer's disease, and/or other neurodegenerative diseases. One embodiment of the multi-component formulation comprises methylsulfonylmethane, at least one energy source component, and at least one of an herbal component or a nutritional component. In one formulation, the energy source component is fructose 1,6-disphosphate. An herbal component of at least one formulation is curcumin. In one further formulation, a nutritional component is selected from the group consisting of docosahexaenoic acid, resveratrol, and blueberry.

5 Claims, 8 Drawing Sheets

(56) References Cited

OTHER PUBLICATIONS

Andrew et al: Social Vulnerability Predicts Cognitive Decline in a Prospective Cohort of Older Canadians. International Conference on Alzheimer's Disease 2006 Poster P3-127.
Ownby et al: Depression and Risk for Alzheimer disease: systematic review, meta-analysis, and metaregression analysis. Archives of General Psychiatry May 2006; 63 (5):530-8. (Abstract Only).
Guskiewicz et al: Association between Recurrent Concussion and Late-Life Cognitive Impairment in Retired Professional Football Players. Neurosurgery Oct. 2005; 57 (4):719-26. (Abstract Only).
Cullen et al: Microvascular Pathology in the Aging Human Brain: Evidence that Senile Plaques are Sites of Microhaemorrhages. Neurobiology of Aging 27 (2006) 1786-1796.
Jefferson et al.: Cardiac Function is Related to Maladaptive Brain Aging in Individuals with Mild Cognitive Impairment: Preliminary Results. International Conference on Alzheimer's Disease 2009 Poster.
Dai et al: Abnormal Regional Cerebral Blood Flow in Cognitively Normal Elderly Subjects with Hypertension. Stroke Feb. 2008; 39:1-6.
Song et al: Hypoxia Facilitates Alzheimer's Disease Pathogenesis. International Conference of Alzheimer's Disease 2006 Poster P4-104.
Dede et al: Endothelial Dysfunction and Alzheimer's Disease. International Conference on Alzheimer's Disease 2006 Poster P4-105.
Aliev et al: Brain Mitochondria as a Primary Target in the Development of Treatment Strategies for Alzheimer's disease. The International Journal of Biochemistry and Cell Biology 2009. (p. 1 Only).
Kivipelto et al: Obesity and Vascular Risk Factors at Midlife and the Risk of Dementia and Alzheimer Disease. Archives of Neurology Oct. 2005; 62 (10):1556-60. (Abstracts Only).
Rusanen et al: Heavy Smoking in Midlife and Long-Term Risk of Alzheimer Disease and Vascular Dementia. Archives of Internal Medicine Feb. 2011; 171 (4):333-339. (Abstract Only).
Rocca: Ovary Removal Surgery Elevates Risk for Dementia. Mayo Clinic Release Apr. 5, 2006.
Kiraly et al: Traumatic Brain Injury and Delayed Sequelae: A Review—Traumatic Brain Injury and Mild Traumatic Brain Injury (Concussion) are Precursors to Later-Onset Brain Disorders, Including Early-Onset Dementia. Scientific World Journal Nov. 12, 2007; 7:1768-76. (Abstract Only).
Yuede et al: Effects of Forced Versus Voluntary Exercise on Cognitive Deficits in Tg2576 Mice. International Conference on Alzheimer's Disease 2006, Poster P1-047. (Abstract Only).
Larson et al: Exercise is Associated with Reduced Risk for Incident Dementia Among Persons 65 Years of Age and Older. Annals of Internal Medicine Jan. 2006; 144 (2):73-81. (Abstract Only).
Kraus et al: Exercise Training, Lipid Regulation, and Insulin Action: A Tangled Web of Cause and Effect. Obesity (Silver Spring) Dec. 2009; 17 (N3S):S21-S26. (Abstract Only).
Valdez et al: Attenuation of Age Related Changes in Mouse Neuromuscular Synapses by Caloric Restriction and Exercise. Proceedings of the National Academy of Sciences Aug. 2010; 17; 107 (33):14863-14868. (Abstract Only).
Shaw : Head to Toe—Daniel Lieberman Tracks the Evolution of the Human Head. Harvard Magazine. Jan.-Feb. 2011, pp. 25, 27-29.
Wilson et al: Chronic Distress and Incidence of Mild Cognitive Imperilment. Neurology Jun. 2007; 68(24): 2085-2092. (Abstract Only).
McKinsey et al: Cerebral Perfusion in Alzheimer's Disease Using Dynamic Susceptibility Contrast MRI. International Conference of Alzheimer's Disease 2008, Poster P2-228. (Abstract Only).
Sowell et al: Assessing Immune-Related Oxidative Stress and Proteomics in a Mouse Model of Alzheimer's Disease. International Conference of Alzheimer's Disease 2008, Poster P4-177. (Abstract Only).
Ridley: Connecting the Pieces of the Alzheimer's Puzzle. Wall Street Journal 2010.
Craik et al: Delaying the Onset of Alzheimer's Disease: Bilingualism as a Form of Cognitive Reserve. Neurology Nov. 2010; 75(19):1726-9. (Abstract Only).
Hotz: Tiny Gene Variations Can Even Alter Effect of the Pills We Take. Wall Street Journal Mar. 21, 2008.
Plumridge : Pharmaceutical Sector Remains Genetically Challenged. Wall Street Journal Jan. 2011.
No Longer Treating Different Conditions Identically. Roche Nachrichten Oct. 2008.
Roche Personalised Healthcare—In Brief. F. Hoffmann-La Roche AG. Dec. 2010.
Prasad et al: Multiple Antioxidants in the Prevention and Treatment of Neurodegenerative Disease: Analysis of Biologic Rationale. Current Opinion in Neurology Dec. 1999; 12 (6):761-770.
Grundman et al: Antioxidant Strategies for Alzheimer's Disease. Proceedings of Nutrition Society May 2002; 61(2):191-202. (Abstract Only).
Impact of a 5-Year Delayed Onset of AD Due to a Treatment Breakthrough. Alzheimer's Association Website Accessed Jun. 30, 2010.
De La Torre: Alzheimer's Disease is Incurable but Preventable. Journal of Alzheimer's Disease 2010.
Dartigues: Prodromal Alzheimer's Disease: Data from the PAQUID Study. International Conference of Alzheimer's Disease 2009, Presentation S4-02-04. (Abstract Only).
Fackelmann : 18% of All Boomers Expected to Develop Alzheimer's. USA Today Mar. 18, 2008.
Gabryelewicz et al: Conversion to Dementia Over a Five Year Period Among Patients with Mild Cognitive Impairment in Polish Follow-Up Study. International Conference of Alzheimer's Disease 2008 Poster P1-189. (Abstract Only).
Jacob et al: Pharmacology of Dimethyl Sulfoxide in Cardiac and CNS Damage. Pharmacological Reports 2009; 61:225-235.
Regoli et al: Quantification of Total Oxidant Scavenging Capacity of Antioxidants for Peroxynitrite, Peroxyl Radicals, and Hydroxyl Radicals. Toxicology and Applied Pharmacology 1999; 156:96-105. (p. 96 and One Unnumbered Page Only).
Camici et al: Dimethyl Sulfoxide Inhibits Tissue Factor Expression, Thrombus Formation, and Vascular Smooth Muscle Cell Activation. Circulation 2006; 114:1512-1521. (p. 1512 Only).
Tatzelt et al: Chemical Chaperones Interfere with the Formation of Scrapie Prion Protein. EMBO Journal Dec. 1996; 15(23):6363-6373. (Abstract Only).
De La Torre et al: Reversal of Ischemic-Induced Chronic Memory Dysfunction in Aging Rats with a Free Radical Scavenger-Glycolitic Intermediate Combination. Brain Research 1998; 779:285-288. (First Page Only).
Karaca et al: Ischemic Stroke in Elderly Patients Treated with a Free Radical Scavenger-Glycolytic Intermediate Solution: a Preliminary Pilot Trial. Neurological Research Jan. 2002; 24 (1):73-80. (Abstract and p. 73 Only).
Bardutzky et al: Effects of Intravenous Dimethyl Sulfoxide on Ischemia Evolution in a Rat Permanent Occlusion Model. Journal Cerebral Blood Flow Metabolism Aug. 2005; 25 (8):968-77. (Abstract Only).
Kalt et al: Effect of Blueberry Feeding on Plasma Lipids in Pigs. British Journal of Nutrition Nov. 2007. (p. 1 of 9 Only).
Ebewe Pharma Ges, Investigator's Brochure, Cerebrolysin in Dementia. May 2003. (Cover Only).
Alvarez et al: A 24-Week, Double-Blind Placebo-Controlled Study of Three Dosages of Cerebrolysin in Patients with Mild to Moderate Alzheimer's Disease. European Journal of Neurology Jan. 2006; 13(1):43-54. (Abstract Only).
Alvarez et al: Neuropeptide Dietary Supplement N-PEP-12 Enhances Cognitive Function and Activates Brain Bioelectrical Activity in Healthy Elderly Subjects. Methods Find Exp Clin Pharmacol. Sep. 2005; 27 (7):483-87. (Abstract Only).
Brain Energizer: A Randomized, Double-Blind, Placebo-Controlled Trial, Changchung City 2nd Hospital, China 1997.
Chohan et al: Enhancement of Dentate Gyrus Neurogenesis, Dendritic and Synaptic Plasticity and Memory by Neurotrophic Peptide. Neurobiology of Aging Aug. 2011; 32(8):1420-34. (Abstract Only).

(56) References Cited

OTHER PUBLICATIONS

Egleton et al: Development of Neuropeptide Drugs that Cross the Blood Brain Barrier. NeuroRx Jan. 2005; 2(1):44-53. (pp. 44 and 50 Only).
Ali et al: Dealing with Misfolded Proteins; Examining the Neuroprotective Role of Molecular Chaperones in Neurodegeneration. Molecules 2010;15:6859-6887. (pp. 6859-6874 Only).
Zhai et al: NAD Synthase NMNAT Acts as a Chaperone to Protect Against Neurodegeneration. Nature Apr. 2008; V452:887-891.
Chiu et al: Up-regulation of Crystallins is involved in the neuroprotective effect of wolfberry on survival of retinal ganglion cells in rat ocular hypertension model. Journal of Cellular Biochemistry Mar. 2010; 110:311-320.
Windisch et al: Role of Alpha-Synuclein in Neurodegenerative Diseases: A Potential Target for New Treatments Strategies? Neurodegenerative Diseases 2008; 5:218-221.
Blair et al: In Vivo Administration of Heat Shock Protein 27 Variants; Implications for tauopathies. Society for Neuroscience 2009, Program 600.3. (Abstract Only).
Cavallucci et al: HSP70 Deregulation in a Mouse Model of Alzheimer's Disease: A Potential Mechanism for Early Synaptic Deficit. Society for Neuroscience 2009. Poster B117. (Abstract Only).
Wieten et al: HSP70 expression and induction as a readout for detection of immune modulatory components in food. Cell Stress and Chaperones (2010) 15:25-37. (pp. 25-33 Only).
O'Leary et al: Chemically Tuning Tau Fate Decisions with Chaperone Modulators. Society for Neuroscience 2009. Program 600.2. (Abstract Only).
Ali et al: Nicotinamide Mononucleotide Adenylyltransferase is a Stress Response Protein Regulated by the HFS/HIF1A {alpha} Pathway. Journal of Biological Chemistry May 2011; 286(21):19089-99. (Abstract Only).
Aggarwal et al: Curcumin—Biological and Medicinal Properties. Turmeric: The Genus *Curcuma* 2006 Chapter 10. (pp. 297-298, 329-330 Only).
Teiten et al: Induction of Heat Shock Response by Curcumin in Human Leukemia Cells. Cancer Letters Jul. 2009; 279 (2):145-54. (Abstract Only).
Ma et al: Beta-Amyloid Oligomers Induce Phosphorylation of Tau and Inactivation of Insulin Receptor Substrate via c-Jun N-Terminal Kinase Signaling: Suppression by Omega 3 Fatty Acids and Curcumin. Journal of Neuroscience Jul. 2009; 29 (28):9078-9089. (Abstract and pp. 9078-9089).
Saw et al: Synergistic Anti-Inflammatory Effects of Low Doses of Curcumin in Combination with Polyunsaturated Fatty Acids: Docosahexaenoic Acid or Eicosapentaenoic Acid. Biochemical Pharmacology Feb. 2010; 79(3):421-430. (Abstract Only).
Napryeyenko et al: Ginkgo Biloba Special Extract in Dementia with Neuropsychiatric Features. A Randomized, Placebo-Controlled, Double-Blind Clinical Trial. Arzneimittelforschung 2007; 57(1):4-11. (Abstract Only).
Kim et al: Alzheimer's Disease Drug Discovery from Herbs. Journal of Alternative and Complementary Medicine 2007; 13(3):333-340. (Abstract and Complete Article).
Zhou et al: Clinical Study on Effect of Shenyin Oral Liquid in Treating Mild Cognitive Impairment. Zhongguo Zhong Xi Yi Jie He Za Zhi Sep. 2007; 27(9):793-5. (Abstract Only).
Li et al: Pharmacological Studies of Traditional Chinese Medicine to Treat Alzheimer's Disease. International Conference on Alzheimer's Disease 2006. Poster P4-273.
Chang et al: Development of Gouqizi (*Lycium barbarum*) as Neuroprotective Agents. The University of Hong Kong, Aug. 2005. (pp. 1-4, 6, 7-9).
Chang et al: Medicinal and Nutraceutical Uses of Wolfberry in Preventing Neurodegeneration in Alzheimer's Disease. Recent Advances on Nutrition and the Prevention of Alzheimer's Disease. 2010; 169-185.

Ho et al: Anti-Aging Herbal Medicine—How and Why Can They be Used in Aging Associated Neurodegenerative Diseases? Aging Research Reviews 9 (2010) 354-362.
Chang et al: Use of Anti-Aging Herbal Medicine, *Lycium barbarum*, Against Aging Associated Diseases. What Do We Know So Far? Cell Mol Neurobiol Jul. 2007.
Qin et al: Neuronal SIRT1 Activation as a Novel Mechanism Underlining the Prevention of Alzheimer's Disease Amyloid Neuropathology by Calorie Restriction. Journal of Biological Chemistry Jun. 2006. Abstract and Poster.
Morillo et al: Obesity and Cognition in an Interdisciplinary Program to Treat Aged Women Obesity. International Conference on Alzheimer's Disease 2008. Poster P2-117. (Abstract Only).
Lombardo et al: Memory Preservation Diet for Reducing Risk and Slowing Progression of Alzheimer's Disease. International Conference on Alzheimer's Disease 2006. Poster P-157.
Scarmeas et al: Mediterranean Diet and Risk for Alzheimer's Disease. Annals of Neurology Jun. 2006; 59(6):912-921. (Abstracts Only).
Laitinen et al: Fat Intake at Midlife and Cognitive Impairment Later in Life: A Population Based Study. International Conference on Alzheimer's Disease 2006. Poster P3-125.
Wolfe et al: Cellular Antioxidant Activity of Common Fruits. Journal of Agricultural and Food Chemistry. Jul. 2008.
Krikorian et al: Blueberry Supplementation Improves Memory in Older Adults. Journal of Agricultural and Food Chemistry. Jan. 2010.
Spencer: The Impact of Fruit Flavonoids on Memory and Cognition. British Journal of Nutrition (2010), 104:S40-S47.
Malin et al: Short-Term Blueberry-Enriched Diet Prevents and Reverses Object Recognition and Memory Loss in Aging Rats. Nutrition 27 (2011) 338-342. (First Page Only).
Qin et al: Cinnamon: Potential Role in the Prevention of Insulin Resistance, Metabolic Syndrome and Type 2 Diabetes. Journal of Diabetes Science and Technology. May 2010; 4(3):685-693. (Abstract and Complete Article).
Anderson: Chromium and Polyphenols from Cinnamon Improve Insulin Sensitivity. Proceedings Nutrition Society Feb. 2008; 67(1):48-53. (Abstract Only).
Rodrigues et al: Total Oxidant Scavenging Capacity of Euterpe Oleracea Mart. (acai) Seeds and Identification of their Polyphenolic Compounds. Journal of Agricultural Food Chemistry. Jun. 2006; 54 (12):4162-7. (Abstract Only).
Ignarro et al: Pomegranate Juice Protects Nitric Oxide Against Oxidative Destruction and Enhances the Biological Actions of Nitric Oxide. Nitric Oxide. Sep. 2006; 15 (2):93-102. (Abstract and First Page Only).
Hartman et al: Pomegranate Juice Decreases Amyloid Load and Improves Behavior in a Mouse Model of Alzheimer's Disease. Neurobiol Dis. Sep. 27, 2006. (Abstract Only).
Maczurek et al: Lipoic Acid as an Anti-Inflammatory and Neuroprotective Treatment for Alzheimer's Disease. Advance Drug Delivery Review. Jul. 2008. (Abstract Only).
Sharma et al: Effect of Alpha Lipoic Acid, Melatonin and Trans Resveratrol on Intracerebroventricular Streptozotocin Induced Spatial Memory Deficit in Rats. Indian Journal of Physiology. Oct. 2005; 49(4):395-402. (Abstract Only).
Putics et al: Resveratrol Induces the Heat-Shock Response and Protects Human Cells From Severe Heat Stress. Antioxidant Redox Signal. Jan. 2008; 10(1):65-75. (Abstract Only).
Ladiwala et al: Resveratrol Selectively Remodels Soluble Oligomers and Fibrils of Amyloid Abeta into Off-Pathway Conformers. J Biol Chem. Jul. 2010; 285 (31):24228-37. (Abstract Only).
Kennedy et al: Effects of Resveratrol on Cerebral Blood Flow Variables and Cognitive Performance in Humans: A Double-Blind, Placebo-Controlled, Crossover Investigation. American Journal of Clinical Nutrition Jun. 2010; (6):1590-7. (Abstract and Complete Article).
Baur et al: Resveratrol Improves Health and Survival of Mice on a High Calorie Diet. Nature. Nov. 2006. (Abstracts Only).
Chao et al: Dietary Oxyresveratrol Prevents Parkiansonian Mimetic 6-Hydroxydopamine Neurotoxicity. Free Radical Biology and Medicine 2008; 45:1019-1026. (First Page Only).

(56) References Cited

OTHER PUBLICATIONS

Solfrizzi et al: Alcohol Consumption, Mild Cognitive Impairment, and Progression to Dementia. Neurology. May 2007; 68(21):1790-9. (Abstract Only).
Das: Folic Acid and Polyunsaturated Fatty Acids Improve Cognitive Function and Prevent Depression, Dementia, and Alzheimer's Disease—But How and Why? Prostaglandins Leukot Essent Fatty Acids. Jan. 2008; 78(1):11-9. (Abstract Only).
Tchantchou et al: Dietary Supplementation with Apple Juice Concentrate Alleviates the Compensatory Increase in Glutathione Synthase Transcription and Activity that Accompanies Dietary- and Genetically-Induced Oxidative Stress. Journal of Nutritional Health & Aging. 2004; 8(6):492-6. (Abstract Only).
Suh et al: Pharmacological characterization of orally active cholinesterase inhibitory activity of *Prunus persica* L. Batsch in rats. Journal of Molecular Neuroscience. 2006; 29(2):101-7. (Abstract Only).
Shukitt-Hale et al: Walnuts can improve motor and cognitive function in aged rats. Society for Neuroscience 2007. Poster N24. (Abstract Only).
Chauhan et al: Walnut Extract Inhibits the Fibrillization of Amyloid Beta-Protein, and Also Defibrillizes its Preformed Fibrils. Current Alzheimer Research. Aug. 2004; 1(3):183-8. (Abstract Only).
Cao et al: Caffeine Synergizes with Another Coffee Component to Increase Plasma GCSF: Linkage to Cognitive Benefits in Alzheimer's Mice. Journal of Alzheimer's Disease. 2011; 25(2):323-35. (Abstract Only).
Frautschy et al: What was lost in translation in the DHA trial is whom you should intend to treat. Alzheimer's Research & Therapy. 2011, 3:2.
Jicha et al: Omega-3 Fatty Acids: Potential Role in the Management of Early Alzheimer's Disease. Clinical Interventions in Aging. 2010:5 45-61.
Yurko-Mauro et al: Beneficial Effects of Docosahexaenoic Acid on Cognition in Age-Related Cognitive Decline. Alzheimer's & Dementia 2010:1-9.
Eckert et al: Plant Derived Omega-3 Fatty Acid Modulate Fatty Acid Composition in the Brain and Provide Neuroprotective Properties. Society for Neuroscience. 2008. Poster M10. (Abstract Only).
Muldoon et al: Serum Phospholipid Docosahexaenoic Acid is Associated with Cognitive Functioning during Middle Adulthood. Journal of Nutrition. Feb. 24, 2010. (Summary Only).
Heo et al: Protective Effects of Quercetin and Vitamin C Against Oxidative Stress-Induced Neurodegeneration. Journal of Agricultural Food Chemistry. Dec. 2004; 52(25):7514-17. (Abstract Only).
Ho et al: Isolation and Characterization of Grape-Derived Polyphenolic Extracts with Abeta-Lowering Activity That Could be Developed for Alzheimer's Disease. Society for Neuroscience 2007. Program 548.7. (Abstract Only).
Dragicevic et al: Green Tea Epigallocatechin-3-Gallate (EGCG) and Other Flavonoids Reduce Alzheimer's Amyloid Induced Mitochondrial Dysfunction. Journal of Alzheimer's Disease 26 (2011) 507-521. (pp. 507-509 Only).
Collins et al: Watermelon Consumption Increases Plasma Arginine Concentrations in Adults. Nutrition. Mar. 2007; 23(3):261-6. (Abstract Only).
Tabet et al: Endogenous Antioxidant Activities in Relation to Concurrent Vitamins A, C, and E Intake in Dementia. International Psychogeriatrics. Mar. 2002; 14(1):7-15. (Abstract Only).
Richards et al: Higher Serum Vitamin D Concentrations are Associated with Longer Leukocyte Telomere Length in Women. American Journal of Clinical Nutrition. Nov. 2007; 86(5):1420-1425. (Abstract Only).
Yang et al: Coenzyme Q10 Attenuates Hyperphosphorylation of Tau With Up-Regulation of AKT Signaling in the Aged Transgenic Mice with Alzheimer Presenilin 1 Mutation. International Conference on Alzheimer's Disease 2008. Poster P2-158. (Abstract Only).
Kamphuis et al: Can Nutrients Prevent or Delay Onset of Alzheimer's Disease? Journal of Alzheimer's Disease 20 (2010) 765-775.

Parachikova et al: Formulation of a Medical Food Cocktail for Alzheimer's Disease. Beneficial Effects on Cognition and Neuropathology in a Mouse Model of the Disease. PLoS ONE. Nov. 2010; 5(11):e14015.
Beking et al: Flavonoids and Alzheimer's Disease Prevention; An Ecological Analysis of Potential Neuropotective Factors. International Conference on Alzheimer's Disease 2009. Poster.
Chan et al: A Vitamin/Nutriceutical Formulation Improves Memory and Cognitive Performance in Community-Dwelling Adults without Dementia. Journal of Nutritional Health and Aging. 2010; 14(3) 224-30. (Summary Only).
Tohda et al: Kihi-To, a Herbal Traditional Medicine, Improves Abeta(25-35)-Induced Memory Impairment and Losses of Neurites and Synapses. BMC Complementary and Alternative Medicine. Aug. 2008; 8:49. (Abstract Only).
Presley et al: Acute Effect of a High Nitrate Diet on Brain Perfusion in Older Adults. Nitric Oxide. Oct. 2010. (Abstract Only).
De La Torre et al: Inhibition of Vascular Nitric Oxide After Rat Chronic Brain Hypoperfusion: Spatial Memory and Immunocytochemical Changes. Journal of Cerebral Blood Flow & Metabolism (2005) 25, 663-672.
Bondy et al: Retardation of Brain Aging by Chronic Treatment with Melatonin. Annals of The New York Academy of Sciences 2004; 1035:197-215. (pp. 197 and 211 Only).
Wu et al: Hematopoietic Effect of Fractions from the Enzyme-Digested Colla Corii Asini on Mice with 5-Flourouracil Induced Anemia. American Journal of Chinese Medicine 2007; 35(5):853-66. (Abstract Only).
Yao et al: Effects of Ejiao (Colla Corii Asini) on the Hemodynamics, Hemorheology and Microcirculation During Endotoxin Shock in Dogs. Zhongguo Zhong Yao Za Zhi. Jan. 1989; 14(1):44-6, 64. (Abstract Only).
Park et al: Methyl Salicylate is a Critical Mobile Signal for Plant Systemic Acquired Resistance. Science. Oct. 2007; 318:113-116.
Singh et al: Allopregnanolone Reverses the Learning and Memory Deficits of Adult Triple Transgenic Alzheimer's Disease Mice. Society for Neuroscience 2008. Poster AA13. (Abstract Only).
Myung et al: Improvement of Memory by Dieckol and Phlorofucofuroeckol in Ethanol-Treated Mice: Possible Involvement of the Inhibition of Acetylcholinesterase. Archives of Pharmaceutical Research. Jun. 2005; 28(6):691-8. (Abstract Only).
Vosler et al: Calpain-mediated Signaling Mechanisms in Neuronal Injury and Neurodegeneration. Molecular Neurobiology. Aug. 2008; 38(1):78-100. (Abstract Only).
Putics et al: Zinc Supplementation Boosts the Stress Response in the Elderly: Hsp70 Status is Linked to Zinc Availability in Peripheral Lymphocytes. Exp Gerontol. May 2008; 43(5):452-61. (Abstract Only).
Hanson et al: Intranasal Delivery Bypasses the Blood-Brain Barrier to Target Therapeutic Agents to the Central Nervous System and Treat Neurodegenerative Disease. BMC Neuroscience. Dec. 2008; 9 Suppl 3:S5. (Abstract Only).
Silva: Nanotechnology Approaches to Crossing the Blood-Brain Barrier and Drug Delivery to the CNS. BMC Neuroscience. Dec. 2008; 9(Suppl)3:S4. (Complete Article and Abstract).
Patel et al: True Healing Art of Alzheimer's by Holistic Homeopathy. International Conference of Alzheimer's Disease 2006. Poster P1-448.
Mattson et al: Neurohormetic Phytochemicals: Low Dose Toxins that Induce Adaptive Neuronal Stress Responses. Trends in Neuroscience. Sep. 2006; 29(11). (Incomplete).
Lonsdorf et al: Neurological Understanding of Ayurvedic Medicine and its Application to Dementia Prevention. International Conference on Alzheimer's Disease 2006. Poster P-168.
Goldsmith: Treatment of Alzheimer's Disease by Transposition of the Omentum. Annals of The New York Academy of Science 2002. 977:456-467. (p. 454 Only).
Du et al: The Effect of Moxibustion on Spatial Memory of Aging Rats and the Underlying Mechanisms. International Conference on Alzheimer's Disease 2006. Poster P4-415.
Zoladz et al: Cognitive Enhancement Through Stimulation of the Chemical Senses. North American Journal of Psychology 2005; 7(1). (First Page Only).

(56) References Cited

OTHER PUBLICATIONS

Rickard et al: The Effect of Music on Cognitive Performance: Insight From Neurobiological and Animal Studies. Behavior Cognition Neuroscience Review. Dec. 2005; 4 (4) 235-61. (Abstract Only).

Bauer et al: Photobiomodulation Attenuates CNS Oxidative Stress in an Animal Model of Diabetes. Society for Neuroscience 2008. Poster 26.

Zelinski et al: The IMPACT Study: A Randomized Controlled Trial of a Brain Plasticity-Based Training Program for Age-Related Cognitive Decline. Society for Neuroscience 2007. Poster.

Herrera et al: Human Photosynthesis and its Impact on Alzheimer's and Other Neurodegenerative Diseases. International Conference on Alzheimer's Disease 2008. Poster.

Jeong et al: Environmental Enrichment Compensates the Effects of Stress on the Disease Progression in the Tg2576 Mice, an Alzheimer's Disease Model. Society for Neuroscience 2007. Poster M16. (Abstract Only).

Arendash et al: Environmental Enrichment "Sessions" are Sufficient to Provide Cognitive Benefit to Impaired Alzheimer's Transgenic Mice Without Affecting Brain or Plasma Aβ Levels. International Conference on Alzheimer's Disease 2008. Poster P1-068. (Abstract Only).

Chen: Regulatory Prospects of Botanical New Drugs. Medicine in the 21st Century Tri-Conference & Bio-Forum 2004. Shanghai, China. pp. 220-226.

Chen et al: New Therapies from Old Medicines. Nature Biotechnology. Oct. 2008; 26(10):1077-1083.

Xie: Changing Mind to Match the Feature of TCM for Developing Chromatographic Fingerprint to Assess the Quality of Herbal Medicine. Medicine in the 21st Century Tri-Conference & Bio-Forum 2004. Shanghai, China. pp. 108-109.

U.S. Department of Health and Human Services, Food and Drug Administration, Center for Drug Evaluation and Research (CDER): Guidance for Industry Codevelopment of Two or More Unmarketed Investigational Drugs for Use in Combination *Draft Guidance*. Dec. 2010. Federal Register 75:240:78259.

Mathews: Recent Cases Point to the Limitations of Animal Drug Tests. Wall Street Journal. Mar. 31, 2007.

Banks: Developing Drugs That Can Cross the Blood-Brain Barrier: Applications to Alzheimer's Disease. BMC Neuroscience 2008. 9(Suppl)3:S2.

Patel et al: Getting into the Brain Approaches to Enhance Brain Drug Delivery. CNS Drugs 2009; 23(1):35-52.

Voelker: Guideline: Dementia Drugs' Benefits Uncertain. JAMA Apr. 2008. 299(15):1763.

Neuroscience Under Threat as Big Pharma Backs Off. Reuters News. Feb. 11, 2011.

Zamiska: Dueling Therapies: Is a Shotgun Better than a Silver Bullet. Wall Street Journal. Mar. 2, 2007.

Newman et al: Natural Products as Sources of New Drugs Over the Last 25 Years. Journal Natural Products 2007. 70:461-477. (p. 461 Only).

Johns Hopkins School of Public Health: Alzheimer's Disease to Quadruple Worldwide by 2050. Public Health News Center. Jun. 10, 2007.

De La Torre: Vascular Risk Factor Detection and Control May Prevent Alzheimer's Disease. Aging Research Reviews 2010. 9:218-225. (First Page Only).

De La Torre : Alzheimer Disease as a Vascular Disorder. Stroke 2002. 33:1152-1162.

Chang et al: Significance of Molecular Signaling for Protein Translation Control in Neurodegenerative Diseases. Neuro-Signals 2007. 15:249-258. (pp. 249, 254 and 255 Only).

Vellas: Recommendations and Outcomes of Disease Modifying Drugs. International Conference on Alzheimer's Disease 2008. Presentation S2-04-01. (Abstract Only).

Siemers: Disease Modification: Will We Know It When We See It? International Conference on Alzheimer's Disease 2008. Presentation S2-04-02. (Abstract Only).

Jones et al: Variation in Placebo Decline Across a Decade of Alzheimer's Disease Trials. International Conference on Alzheimer's Disease 2008. Poster.

Rosen et al: Patterns of Aβ Accumulation in Alzheimer's and Aged Primate Brain. International Conference on Alzheimer's Disease 2006. Poster P2-005.

Rosen et al: Tauopathy with Paired Helical Filaments in an Aged Chimpanzee. The Journal of Comparative Neurology. May 2008. 509(3):259-270. (Abstract Only).

Barger: Cooperative Ideas About Cooperative Strategies. Annals of The New York Academy of Science 2004; 1035:350-353. (pp. 350-352 Only).

Ramassamy: Emerging Role of Polyphenolic Compounds in the Treatment of Neurodegenerative Diseases: A Review of Their Intracellular Targets. European Journal of Pharmacology 2006. 545:51-64. (pp. 51, 52 and 60 Only).

Steel: Alzheimer's Disease May Not Be a Disease At All: BMJ Jun. 16, 2006. (Email).

Curtis et al: Human Neuroblasts Migrate to the Olfactory Bulb via a Lateral Ventricular Extension. Science. Feb. 2007. (Abstract Only).

Park : Alzheimer's Unlocked. Time Magazine. Oct. 25, 2010. pp. 53-59.

Passos et al: Feedback Between p21 and Reactive Oxygen Production Is Necessary for Cell Senescence. Molecular Systems of Biology. Feb. 2010; 6:347.

Kad et al: Collaborative Dynamic DNA Scanning by Nucleotide Excision Repair Proteins Investigated by Single-Molecule Imaging of Quantum-Dot-Labeled Proteins. Molecular Cell. Mar. 2010; 37(5):702-713. (Summary Only).

Reuter et al: Epigenetic Changes Induced by Curcumin and Other Natural Compounds. Genes Nutrition. May 2011. 6(2) 93-108. (Abstract Only).

Nabel et al: Demystifying DNA Demethylation. Science. Sep. 2011. 333(6047):1229-1230.

Vogel: Do Jumping Genes Spawn Diversity? Science. Apr. 2011. vol. 332, pp. 300-301.

Department of Veterans Affairs: A Randomized, Clinical Trial of Vitamin E and Memantine in Alzheimer's Disease (TEAM-AD). Oct. 2005.

Anselm et al: Grape Juice Causes Endothelium-Dependent Relaxation Via a Redox-Sensitive Src- and Akt-Dependent Activation of eNOS. Cardiovascular Research Jan. 15, 2007;73(2):404-13. Epub Aug. 8, 2006. (Abstract Only).

Klein et al: Grape-Enriched Diet Upregulates Transthyretin in Aged Mouse Brain: Potential Protection From Alzheimer's Disease? International Conference on Alzheimer's Disease 2007. Poster N27. (Abstract Only).

Räthel et al: Activation of Endothelial Nitric Oxide Synthase by Red Wine Polyphenols: Impact of Grape Cultivars, Growing Area and the Vinification Process. Journal of Hypertension Mar. 2007;25(3):541-9. (Abstract Only).

Pasinetti et al: Grape Seed Polyphenolic Extracts (GSPE) as a Potential Novel Treatment in Progressive Supranuclear Palsy: Experimental Approaches and Therapeutic Implications. Program No. 600.4. Society for Neuroscience 2009. (Presentation Abstract).

Chao et al: Novel Neuroprotective Effects of Oxyresveratrol Preventing 6-Hydroxydopamine-Induced Neurotoxicity: Antioxidant Activity and Up-Regulation of sirt1. Poster No. X5. Society for Neuroscience 2008. (Presentation Abstract).

Ljungberg et al: CREB-Activity and nmnat2 Transcription are Down-Regulated Prior to Neurodegeneration, while NMNAT2 Over-Expression is Neuroprotective, in a Mouse Model of Human Tauopathy. Human Molecular Genetics. Oct. 25, 2011; 21(2):251-267. (Abstract Only).

Ali et al: NMNAT Suppresses Tau-Induced Neurodegeneration by Promoting Clearance of Hyperphosphorylated Tau Oligomers in a *Drosophila* Model of Tauopathy. Human Molecular Genetics. Sep. 30, 2011; 21(2):237-250. (Abstract Only).

Piau et al: Progress in the Development of New Drugs in Alzheimer's Disease. Journal of Nutrition, Health & Aging. 2011;15(1):45-57. (p. 45 Only).

(56) References Cited

OTHER PUBLICATIONS

Wen et al: Nmnat Exerts Neuroprotective Effects in Dendrites and Axons. Molecular and Cellular Neurosciences. Sep. 2011; 48(1):1-8. Epub May 9, 2011. (Abstract Only).

Holtzman et al: Alzheimer's Disease: The Challenge of the Second Century. Science Translational Medicine. Apr. 6, 2011; 3(77): 77sr1 . (pp. 1 and 12 Only).

U.S. Department of Health and Human Services, Food and Drug Administration, Center for Drug Evaluation and Research (CDER): Guidance for Industry Codevelopment of Two or More Unmarketed Investigational Drugs for Use in Combination. Dec. 2010.

Liang: On Fingerprinting Techniques for Quality Control of TCM. Medicine in the 21st Century Tri-Conference & Bio-Forum 2004. Shanghai, China. pp. 76-78 and 87.

Aggarwal et al: Curcumin: The Indian Solid Gold. Adv Exp Med Biol. 2007;595:1-75. (Abstract Only).

Bin Li et al: Enhancement of Dentate Gyrus Neurogenesis and Associated Memory by a Neurotrophic Peptide. Jul. 28, 2008, Poster No. P2-445. (Abstract Only).

Shaw: Fitness: Body and Mind. Harvard Magazine. Nov.-Dec. 2010, pp. 12-13.

Chan et al: Apple Juice Concentrate Maintains Acetylcholine Levels Following Dietary Compromise. Journal of Alzheimer's Disease. Aug. 2006; 9(3):287-91. (Abstract Only).

Gureviciene et al: Amyloid Plaques Confer Neuroprotection Against Exogenous Aβ Oligomers. Society for Neuroscience 2012, Program 748.16/E9. (Abstract Only).

Terracciano et al: Personality and Resilience to Alzheimer's Disease Neuropathology: A Prospective Autopsy Study. Neurobiology of Aging Oct. 2012; (Abstract Only).

Herrmann et al: Uncovering the Proteomic Basis of Mitochondrial Dysfunction in Relation to Alzheimer's Disease. Society for Neuroscience 2012, Program 747.09/D48. (Abstract Only).

Wang: Alzheimer Diagnosis Possible With Scan. Wall Street Journal. Apr. 9, 2012.

Baker et al: Age-Related Learning Deficits Can be Reversible in Honeybees Apis mellifera. Exp Gerontol. Oct. 2012; 47(10):764-72 (Abstract Only).

Panickar: Beneficial Effect of Herbs, Spices, and Medicinal Plants on the Metabolic Syndrome, Brain, and Cognitive Function. Central Nervous System Agents in Medicinal Chemistry, 2013, vol. 13, No. 1 (pp. 1-17).

Codispoti et al: Longitudinal Brain Activity Changes in Asymptomatic Alzheimer Disease. Brain and Behavior 2012. (pp. 221-230).

\* cited by examiner

MULTI-COMPONENT FORMULATIONS FOR THE TREATMENT OF COGNITIVE DECLINE INCLUDING ALZHEIMER'S DISEASE

BACKGROUND OF THE INVENTION

Field of the Invention

This invention relates generally to formulations and methods for treatment, delay, and/or prevention of disease. More in particular, the present invention comprises multi-component formulations and methods for the treatment, delay, and/or prevention of cognitive decline, including Alzheimer's disease, and/or other neurodegenerative diseases.

Description of Related Art

Alzheimer's Disease ("AD") is believed to be a multifactorial degenerative disease rather than the result of a single malfunction or agent. Although AD is usually accompanied by the abnormal accumulation of extracellular deposits or plaques of β-amyloid protein (AB) and intracellular neurofibrillary tangles of tau protein (NFTs), extensive research has not isolated or identified a cause for the accumulation, nor shown that β-amyloid protein or NFTs are the cause rather than effect of AD. In fact, approximately 30 percent of AD patients have no AB plaques or NFTs at death, and approximately 30 percent of cognitively normal adults do have AB plaques and NFTs at death. AB plaques may even be protective against harmful soluble AB oligomers. (Exhibit 1). Instead, clinical and epidemiological studies have identified numerous contributing factors to AD (Exhibit 2).

Many of the pathologic characteristics of AD, inflammation, oxidative stress, impaired cerebral blood flow and glucose utilization, result from body imbalances, including stress, obesity, and an overloaded immune system (Exhibit 4). In addition, AD has a lengthy, non-linear, accelerating, and degenerative prodromal time period with ample opportunity for preventive intervention, and about 95 percent of AD cases are sporadic late-onset.

PHA-57 is a patented drug which combines dimethyl sulfoxide (DMSO) and fructose 1,6-disphosphate (FDP) (Exhibit 8). DMSO and FDP are small and naturally occurring molecules. PHA-57 can be introduced into the body orally or by injection. DMSO, by itself and in combination with FDP, has many desirable effects (Exhibit 9). It is a powerful antioxidant (Exhibit 10). It supplies energy in the form of ATP. It increases cerebral blood flow without altering blood pressure when significant cell damage is present. It inhibits neuronal cell death after central nervous system injury. It protects against blood clotting (Exhibit 11). It counters calcium dysregulation (Exhibit 54). It is a chemical chaperone which has reduced protein misfolding in prion diseases (Exhibit 12, Exhibit 18). PHA-57 has reversed memory dysfunction in rats. It has shown safety and efficacy in a clinical trial with humans for stroke. DMSO alone has demonstrated efficacy with rats as a neuroprotectant for stroke (Exhibit 13).

Cerebrolysin is a proprietary drug which is a mixture of brain peptides, i.e., proteins and amino acids. It is derived from pigs, which have genetic and other similarities to humans (Exhibit 14). Cerebrolysin is not patented and has been in worldwide use for over 25 years. It is approved for use for AD in more than 30 countries, although not the United States. Cerebrolysin is both neurotrophic and neuroprotective. It is administered by injection, although a weaker derivative of it has been administered orally in pill form and is sold as a dietary supplement in the United States. Cerebrolysin has been shown in numerous trials over time to be both safe and effective (Exhibit 15).

The composition known as the Brain Energizer (Changlong Bio-pharmacy, China; distributed by Glory Medicine and Healthcare Co. Ltd., Hong Kong), is similar to cerebrolysin in that it is made from processed porcine brain peptides. The Brain Energizer is different than cerebrolysin in that it is in powder/pill form, is taken orally, and includes several herbal ingredients. The Brain Energizer demonstrated efficacy without safety problems in a Chinese clinical trial with humans for dementia (Exhibit 16).

There is no clinical evidence as to how cerebrolysin or the Brain Energizer work. PHA-57, cerebrolysin, and the Brain Energizer have all proven to have minimal side effects. The disadvantage of cerebrolysin and the Brain Energizer is that they are both animal (porcine) products, which are susceptible to spreading disease, both in reality and perception.

An equally efficacious and potentially superior alternative is an artificially designed natural neuroprotective protein (Exhibit 17). The most promising alternative by far is the exogenous stimulation of endogenous neuroprotective proteins, including but not limited to nicotinamide mononucleotide adenylyl transferase ("NMNAT"), heat shock proteins, synucleins, crystallins, and other neuronal molecular chaperones. These proteins repair protein misfolding, counter tauopathy, boost immunity, exert neuroprotective effects in dendrites and axons, and are positively associated with recovery brain plasticity in honeybees. (Exhibit 18, Exhibit 12, Exhibit 19, Exhibit 30, Exhibit 57, Exhibit 73).

Furthermore, there are numerous herbals which exhibit various effects. Some herbals are known to strengthen the immune system, increase circulation, provide antioxidant and anti-inflammatory effects, and directly affect and protect neurons before, during, and after stress and injury. Some herbal ingredients are known as herbal enhancers, that is, they improve the efficacy of other herbals when administered in combination. Herbals can be used individually, in combination, or by extracting the active ingredient. Herbals have been tested in the laboratory and clinically in animals and humans. However, clinical and scientific trials with herbals are relatively new, and herbal use is primarily traditional. The widespread traditional use of herbals does indicate safety.

Herbals are the ideal complementary component. Historically, herbals have been used in combination, are not overwhelmingly potent, and are time-tested. Herbals are natural transporters which can help with drug delivery. Herbals are known to be used with the Brain Energizer.

A primary issue with regard to administration of herbals is which herbal or herbals to use. Curcumin has shown extensive anti-inflammatory and neuroprotective properties, and the ability to regulate insulin and glucose uptake (Exhibit 19). *Ginkgo biloba* and its extracts have shown promise (Exhibit 20). Other herbs have produced positive results (Exhibit 21).

Current research on several herbal extracts, focusing on the traditional Chinese medicine, *Lycium barbarum* and its fruit, wolfberry, has shown extensive and varied neuroprotective effects (Exhibit 22, Exhibit 18).

Foods are only a step away from herbals. Proper diet, including calorie restriction and weight loss (Exhibit 23), is an element both of overall health and AD prevention (Exhibit 24). However, for certain nutrients there is a more direct link.

Blueberries contain numerous anthocyanins, including callistephin and kuroman, which preserve mitochondrial structure. Blueberries have demonstrated antioxidant and anti-inflammatory effects which retard brain aging in rats and improve memory in older adults (Exhibit 25).

Cinnamon contains a variety of polyphenols which reduce free radicals, preserve mitochondrial membranes, halt glutamate decline, and modulate immune response and inflammation. Cinnamon has also improved metabolic syndrome and insulin metabolism, and insulin dysfunction has been linked to AD (Exhibit 26).

Acai has exhibited powerful antioxidant capacity (Exhibit 27). Pomegranate juice has shown the ability to protect and enhance the activity of nitric oxide, in addition to neuroprotective effects in both adult and neonatal mice brains (Exhibit 28).

Alpha lipoic acid, by itself and in combination with melatonin and trans-resveratrol, has shown antioxidant and anti-inflammatory effects which slowed the progression of early stage AD, and in combination with exercise, has improved spatial learning and memory in mice (Exhibit 29, Exhibit 3). Resveratrol, which is found in red grapes and wine, has increased cerebral blood flow in healthy adults, evidenced strong antioxidant, anti-inflammatory, and neuroprotective activity and β-amyloid degradation, shown anti-obesity and anti-aging effects in various organisms other than humans, and together with catechin demonstrated synergistic protective action against β-amyloid. Resveratrol has also shown the ability to stimulate neuroprotective proteins and epigenetic effects (Exhibit 30, Exhibit 18, Exhibit 73).

Oxyresveratrol, which is found in mulberry and has one more hydroxyl group than resveratrol, is a stronger antioxidant than resveratrol, with superior neuroprotection and lower toxicity in patient's with AD, stroke, and Parkinson's disease (Exhibit 31).

Moderate consumption of alcohol or wine may slow the rate of progression from mild cognitive impairment to AD in older adults (Exhibit 32).

Folic acid, which stimulates production of docosahexaenoic acid (DHA) and eicosapentaenoic acid (EPA), has decreased homocysteine and improved cognitive function in older adults (Exhibit 33, Exhibit 38).

Apple juice concentrate has produced neuroprotective effects in mice through antioxidant and other mechanisms (Exhibit 34). Peach extract has inhibited acetylcholinesterase in rats (Exhibit 35). Walnut extract, which combines DHA and polyphenols, has shown anti-inflammatory properties, improved cognitive function in aged rats, and inhibited AB fibrillization (Exhibit 36).

Caffeine has reversed cognitive impairment and β-amyloid protein levels in mice (Exhibit 37). Essential fatty acid supplementation, especially omega-3 DHA and including krill oil and plant-derived *perilla* oil, has shown promise for insulin regulation, improved brain health and cognition in non-demented adults, and AD prevention, along with anti-inflammatory and antioxidant effects.

The human brain is 50 percent to 60 percent lipids, primarily DHA. DHA predominates in the metabolically active gray matter and is an essential element of neuronal membranes and neurotransmission, but decreases with age because of oxidation. Fish oil, including EPA, is an anticoagulant which may increase blood flow and the supply of nutrients to the brain and assist in removing toxic metabolites and proteins which accompany neurodegeneration (Exhibit 38, Exhibit 19).

Quercetin, a flavonoid in fruits and vegetables, has both decreased oxidative stress and inhibited acetylcholinesterase in cells (Exhibit 39).

Grape juice and grape extracts have promoted nitric oxide bioavailability and reduced β-amyloid in human and porcine cells, and have shown antioxidant and anti-inflammatory properties in mice (Exhibit 40).

Epigallocatechin-3-gallate, a component of green tea, has displayed antioxidant neuroprotective effects in rat neurons (Exhibit 41).

Watermelon juice, a source of citrulline, has increased arginine in humans and increased arginine with improved vascular function in diabetic rats (Exhibit 42, Exhibit 47, Exhibit 48).

Vitamins A, C, and E have shown potential to reduce oxidative stress and protect against AD (Exhibit 43). Vitamin D has promoted immune system clearance of AB and has decreased inflammation and aging in human cells, and Vitamin D deficiency has been associated with cognitive decline in elderly adults (Exhibit 44).

Coenzyme Q10 has decreased oxidative stress and NFTs, and restored molecular signaling in mice (Exhibit 45). Multinutrient and multiherbal combinations have shown neuroprotective effects (Exhibit 46).

Vascular nitric oxide, along with its precursors, L-arginine and L-citrulline, is a recognized aid to cerebral blood flow. It has antioxidant, anti-inflammatory, and neuroprotective effects, and it is increased by a high nitrate diet (Exhibit 47). Extensive experiments with nitric oxide have been conducted (Exhibit 48).

Melatonin has demonstrated antioxidant and neuroprotective effects in AD (Exhibit 49).

Colla corii asini, a donkey skin extract from China, often mixed with herbs, has shown the ability to improve microcirculation (Exhibit 50).

Aspirin and Vitamin C in combination have evidenced neuroprotective effects. Aspirin alone, in addition to its multiple health benefits, may also have a possible link from plants to the human immune system and neuroprotection (Exhibit 51).

Allopregnanolone, a metabolite of progesterone, has promoted neurogenesis and cognitive enhancement in mice (Exhibit 52).

Eklonia Cava, an extract of brown algae, has shown antioxidant and anti-inflammatory neuroprotective effects, and has improved memory and inhibited acetylcholinesterase and β-amyloid protein in rodents (Exhibit 53).

Combating calcium dysregulation and excess, a degenerative process leading to plaques both in AD and heart disease, has shown promise (Exhibit 54).

Zinc supplementation has increased neuroprotective protein levels in healthy old adults (Exhibit 55, Exhibit 18).

A variety of techniques have also shown promise for AD, including intranasal delivery, nanotechnology (Exhibit 62), homeopathy, neurohormesis, ayurveda, omental transposition, moxibustion, odor administration, hyperbaric oxygen therapy, music, photobiomodulation, computerized cognition training, and human photosynthesis (Exhibit 56). Environmental enrichment has countered the effects of stress on the cognitive ability of mice, provided cognitive benefits to aged mice without impacting β-amyloid, and has been positively associated with recovery brain plasticity and endogenous neuroprotective proteins in honeybees (Exhibit 57).

The FDA has made new rules for botanicals and has recently approved its first botanical drug (Exhibit 58). The standards for approval are no different than for conventional drugs, but these rules take into consideration the different qualities of herbals. Combining herbals with a conventional drug, which is more familiar, should make the approval process easier. Herbals can be "fingerprinted" and verified in order to assure consistency and overcome the objection that herbals cannot be standardized (Exhibit 59).

On Dec. 15, 2010 the FDA issued a draft guidance entitled "Codevelopment of Two or More Unmarketed Investigational Drugs for Use in Combination". The draft states, in part, that "[r]ecent scientific advances have increased our understanding of the pathophysiological processes that underlie many complex diseases, such as cancer, cardiovascular disease, and infectious diseases. This increased understanding has provided further impetus for new therapeutic approaches that rely primarily or exclusively on combinations of drugs directed at multiple therapeutic targets to improve treatment response and minimize development of resistance" (Exhibit 60).

SUMMARY OF THE INVENTION

In view of the numerous and substantial benefits to be realized from formulations exhibiting efficacy in the prevention, and treatment of one or more of the wide variety of degenerative effects which accompany Alzheimer's disease ("AD"), the present invention is directed to a unique new synergistic multi-component formulation for the prevention, delay, and/or treatment of AD, cognitive decline, and/or other neurodegenerative diseases, which counters the multiple contributing factors to AD, cognitive decline, and/or other neurodegenerative diseases, with a novel combination of complementary remedies.

The complementary components combine drugs and herbals, Eastern and Western thinking, natural molecules and nutrients. All of the components of the present formulation, individually and together, work with the body and brain in order to help the body and brain themselves prevent AD. The present formulation should be combined with proper diet (Exhibit 23, Exhibit 24), sleep, exercise without stress, also the best regulator of insulin sensitivity (Exhibit 3), and social/mental/spiritual outlook and lifestyle, including building up "cognitive reserve" (Exhibit 57), in order to minimize the uniquely human and degenerative nature of AD. Although the human brain makes up only 2 percent of the body's mass, it is an organ of amazing complexity and design which controls the entire body. It has virtually no stored oxygen or glucose, and consumes 20 percent of the body's oxygen and 25 percent of the body's glucose, its sole source of energy. As a result, the human brain is continually on the brink of hypoxia and has an enormous and constant appetite for blood and energy, specifically, as much as 15 percent of the blood and 25 percent of the body's essential energy supply at any moment. Oxygen-glucose deprivation then leads to mitochondrial dysfunction and stimulation of neuroprotective proteins. Many of the pathologic characteristics of AD inflammation, oxidative stress, impaired cerebral blood flow and glucose utilization—result from body imbalances, including stress, obesity, and an overloaded immune system.

The formulations of the present invention can help to restore the body's proper balance, and proper lifestyle can help to maintain that balance. The present invention provides a multi-component formulation for the prevention, delay, and/or treatment of Alzheimer's disease, cognitive decline, and/or other neurodegenerative diseases.

In one embodiment, the formulation comprises dimethyl sulfoxide (DMSO), at least one energy source component, at least one herbal component, and at least one nutritional component. In some embodiments of the present invention, the amount of the dimethyl sulfoxide component is in the range of about 5% to about 20% by weight (w/w) of the total formulation.

In at least one embodiment, the at least one energy source component of the formulation of the present invention comprises fructose-6-phosphate. In other embodiments, the at least one energy source component comprises fructose 1,6-disphosphate. In yet another embodiment, the at least one energy source component comprises a combination of fructose-6-phosphate and fructose 1,6-disphosphate. In yet another embodiment, the at least one energy source component comprises glyceraldehyde-3-phosphate. In at least one further embodiment, the amount of the at least one energy source component is about 5% to about 20% (w/w) of the total formulation.

The at least one herbal component in at least one embodiment of the formulation of the present invention comprises curcumin. In another embodiment, the at least one herbal component comprises wolfberry or *Ningxia gouqizi*. In another embodiment, the at least one herbal component comprises cinnamon. In yet another embodiment, the at least one herbal component comprises a combination of components selected from the group consisting of *ginkgo biloba*, ginger, *ginseng*, garlic, wolfberry, *Ningxia gouqizi*, cinnamon and curcumin.

In at least one embodiment, the amount of the at least one herbal component is in the range of about 10% to about 20% (w/w) of the total formulation.

In at least one further embodiment, the at least one nutritional component of the formulation of the present invention comprises an omega-3 fatty acid. In another embodiment, the omega-3 fatty acid comprises docosahexaenoic acid. In a further embodiment, the at least one nutritional component comprises blueberry, and another embodiment, the at least one nutritional component comprises cinnamon. In another embodiment, the at least one nutritional component comprises resveratrol. In yet another further embodiment, the at least one nutritional component is a combination of components selected from the group consisting of omega-3 fatty acid, resveratrol, blueberry, acai, pomegranate juice, alph-lipoic acid, oxyresveratrol, folic acid, apple juice, peach extract, walnut extract, caffeine, quercetin, grape juice, grape extract, epigallocatechin-3-gallate, watermelon juice, vitamin A, vitamin C, vitamin E, vitamin D, coenzyme Q10, and combinations thereof. In at least one embodiment, the amount of the at least one nutritional component of the present invention is in the range of about 50% to about 75% (w/w) of the total formulation. In another embodiment, the amount of a combination of nutritional components of the present invention is in the range of about 50% to about 75% (w/w) of the total formulation.

In at least one embodiment, wolfberry or *Ningxia gouqizi* comprises about 0.1% to about 1% (w/w) of the total formulation. In at least one embodiment, curcumin comprises about 1% to about 10% (w/w) of the total formulation. In at least one embodiment, cinnamon comprises about 5% to about 20% (w/w) of the total formulation. In at least one embodiment, omega-3 fatty acid, such as, but not limited to, docosahexaenoic acid, comprises about 10% to about 40% (w/w) of the total formulation. In at least one embodiment, resveratrol comprises about 5% to about 20% (w/w) of the total formulation. In at least one embodiment, blueberry comprises about 10% to about 40% (w/w) of the total formulation.

In a further embodiment of the present formulation, a pharmaceutical composition for the prevention and/or treatment of Alzheimer's disease is provided. In one embodiment, the pharmaceutical composition comprises about 5% to about 20% (w/w) dimethyl sulfoxide, about 5% to about 20% (w/w) of at least one energy source component, about 10% to about 20% (w/w) of at least one herbal component, and about 50% to about 75% (w/w) of at least one nutritional component. In some embodiments, the pharmaceutical composition is in an oral dosage form.

At least one alternate embodiment of the present invention comprises a multi-component formulation for treatment of neurodegenerative disease. In one embodiment, the formulation comprises methylsulfonylmethane, at least one energy source component, and at least one of an herbal component or a nutritional component. In at least one embodiment, methylsulfonylmethane comprises about 0.01% to about 5% by weight of the total formulation. In one further embodiment, the at least one energy source component comprises about 5% to about 20% by weight of the total formulation. In yet another embodiment, the at least one energy source component comprises about 75% to about 99% by weight of the total formulation.

At least one embodiment of the multi-component formulation for treatment of neurodegenerative disease comprises the at least one herbal component in about 0.01% to about 5% by weight of the total formulation. In another embodiment, the at least one nutritional component comprises about 75% to about 95% by weight of the total formulation. In yet one further embodiment, of the present multi-component formulation, the at least one nutritional component comprises about 0.01% to about 20% by weight of the total formulation.

The present invention is also directed to a multi-component formulation for treatment of cognitive decline. In one embodiment, the multi-component formulation comprises methylsulfonylmethane, fructose 1,6-disphosphate, and at least one of an herbal component or a nutritional component. Methylsulfonylmethane, in at least one embodiment, comprises about 0.01% to about 5% by weight of the total formulation. The nutritional component in at least one embodiment of the present multi-component formulation is selected from the group consisting of docosahexaenoic acid, resveratrol, and blueberry. Fructose 1,6-disphosphate comprises about 5% to about 20% by weight of the total formulation in at least one embodiment, and resveratrol comprises about 75% to about 95% by weight of the total formulation.

In another embodiment of the present multi-component formulation, fructose 1,6-disphosphate comprises about 75% to about 99% by weight of the total formulation. In at least one other embodiment, blueberry comprises about 0.01% to about 20% by weight of the total formulation, and in one other embodiment, docosahexaenoic acid comprises about 0.01% to about 10% by weight of the total formulation.

In at least one embodiment of the present multi-component formulation, the herbal component comprises curcumin. In one further embodiment, curcumin comprises about 0.01% to 5% by weight of the total formulation.

The present invention is further directed to a multi-component pharmaceutical composition. At least one embodiment of the multi-component pharmaceutical composition comprises about 0.1% to about 0.5% by weight methylsulfonylmethane, about 5% to about 99% by weight of fructose 1,6-disphosphate, and about 0.01% to about 95% by weight of one of an herbal component or a nutritional component. In one embodiment of the multi-component pharmaceutical composition, the nutritional component comprises resveratrol, and in one further embodiment, the composition comprises about 85% to about 95% by weight of resveratrol. In at least one further embodiment, the multi-component pharmaceutical composition comprises about 5% to 15% by weight of fructose 1,6-disphosphate.

The present invention further comprises a treatment regimen utilizing a multi-component formulation for the treatment, delay, and/or prevention of cognitive decline, including AD, and/or other neurodegenerative diseases. More in particular, the present treatment regimen comprises a dosages schedule for multi-component formulations comprising different components at different times throughout the day. In this manner, any interference or cross-canceling effects of the various components in a multi-component formulation such as, by way of illustration only, curcumin and resveratrol, enter the user's system at different times of the day, to minimize or eliminate any interfering or cancelling effects which may occur when providing both components at the same time.

In this manner, a treatment regiment may be specifically tailored to a user's needs. Specifically, the present treatment regimen provides only the components of the present multi-component formulations which are necessary for the treatment, delay, and/or prevention of cognitive decline, including AD, or other neurodegenerative diseases for a particular person, eliminating those components a particular user does not require.

The formulations and compositions herein described can be used in connection with pharmaceutical, medical, and cosmetic applications, as well as fundamental scientific research and methodologies, as would be identifiable by a skilled person upon reading of the present disclosure. These and other objects, features and advantages of the present invention will become clearer when the detailed description is taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION

Figure 1:
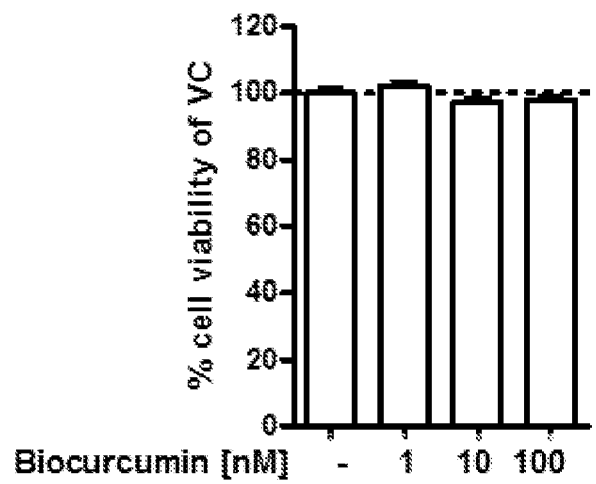
FIG. 1 is a graphical representation of the protective effects of curcumin at various concentrations on primary chicken neurons obtained in accordance with the testing protocols of Example II presented herein.
Figure 2:
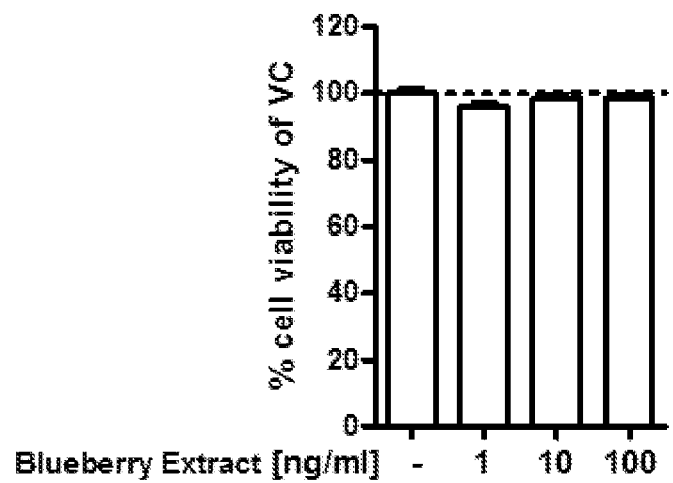
FIG. 2 is a graphical representation of the protective effects of blueberry extract at various concentrations on primary chicken neurons obtained in accordance with the testing protocols of Example II presented herein.
Figure 3:
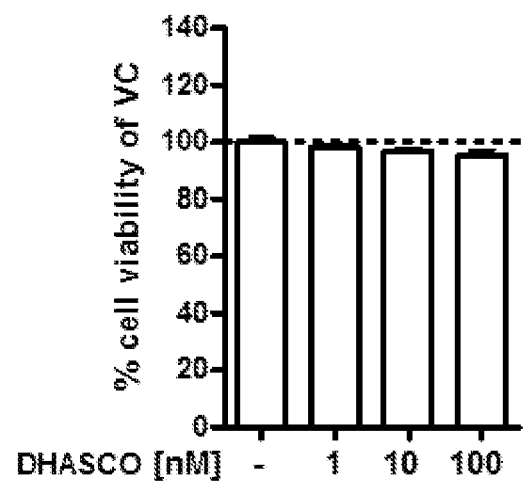
FIG. 3 is a graphical representation of the protective effects of docosahexaenoic acid at various concentrations on primary chicken neurons obtained in accordance with the testing protocols of Example II presented herein.
Figure 4:
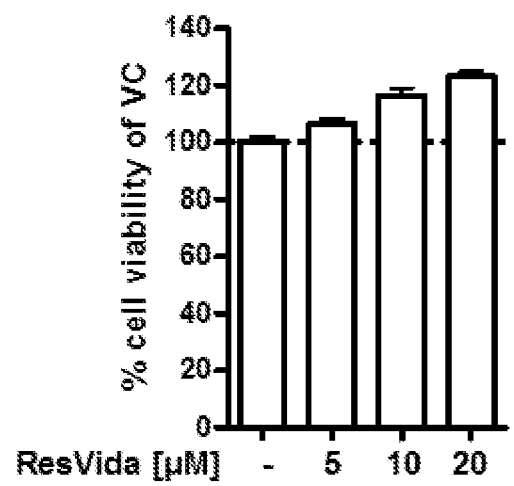
FIG. 4 is a graphical representation of the protective effects of resveratrol at various concentrations on primary chicken neurons obtained in accordance with the testing protocols of Example II presented herein.
Figure 5:
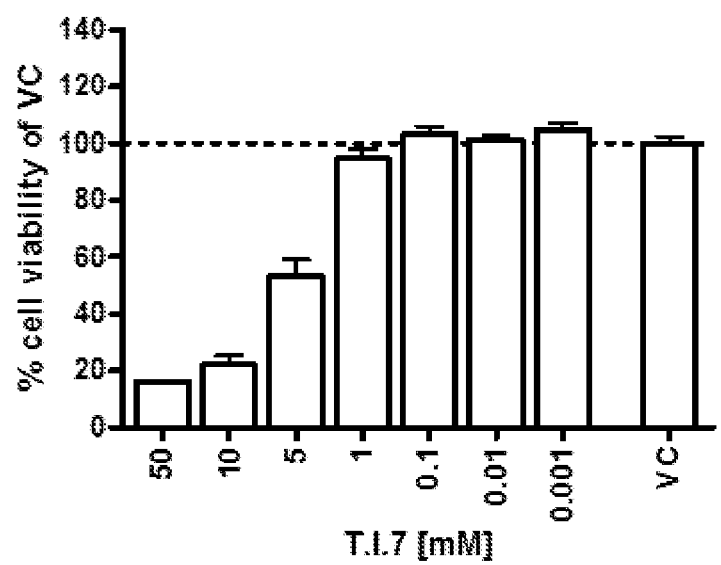
FIG. 5 is a graphical representation of the protective effects of fructose 1,6-disphosphate on primary chicken neurons at various concentrations obtained in accordance with the testing protocols of Example II presented herein.

The present invention is directed to formulations exhibiting therapeutic efficacy for the prevention, delay, and/or treatment of neurodegenerative diseases and/or cognitive decline, including Alzheimer's Disease ("AD").

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, and animals. The present invention is not limited by the illustrated ordering of acts or events, as some acts may occur in different orders and/or concurrently with other acts or events. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting of the invention. As used herein, the indefinite articles "a", "an" and "the" should be understood to include plural reference unless the context clearly indicates otherwise. Further, the singular shall include the plural and the plural shall include the singular, unless specifically stated otherwise.

The phrase "and/or", as used herein, should be understood to mean "either or both" of the elements so conjoined, i.e., elements that are conjunctively present in some cases and disjunctively present in other cases.

As used herein, "or" shall have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of", or, when used in the claims, "consisting of", will refer to the inclusion of exactly one element of a number or list of elements. In general, the term "or" as used herein shall only be interpreted as indicating exclusive alternatives (i.e., "one or the other but not both") when preceded by terms of exclusivity, such as "either", "one of", "only one of", or "exactly one of."

As used herein, the terms "including", "includes", "having", "has", "with", or variants thereof, are intended to be inclusive similar to the term "comprising."

"Formulation" as used herein shall mean and include any collection of components of a compound, mixture, or solution selected to provide optimal properties for a specified end use, including product specifications and/or service conditions. The term formulation shall include liquids, semi-liquids, colloidal solutions, dispersions, emulsions, micro-emulsions, and nanoemulsions, including oil-in-water emulsions and water-in-oil emulsions, pastes, powders, and suspensions. The formulations of the present invention may also be included, or packaged, with other non-toxic compounds, such as cosmetic carriers, excipients, binders and fillers, and the like. Specifically, the acceptable cosmetic carriers, excipients, binders, and fillers contemplated for use in the practice of the present invention are those which render the compounds amenable to oral delivery and/or provide stability such that the formulations of the present invention exhibit a commercially acceptable storage shelf life.

As used herein, the term "subject" refers to any animal (e.g., mammals, birds, reptiles, amphibians, fish), including, but not limited to, humans, non-human primates, rodents, and the like, which is to be the recipient of a particular treatment. Typically, the terms "subject" and "patient" may be used interchangeably herein in reference to a subject. Furthermore, transgenic animals (e.g., transgenic rats and mice) are useful in the methods of the present invention.

As used herein, the term "administering" refers to providing a therapeutically effective amount of a formulation or pharmaceutical composition to a subject, using intravitreal, intraocular, ocular, subretinal, intrathecal, intravenous, subcutaneous, transcutaneous, intracutaneous, intracranial, topical and the like administration. The formulation or pharmaceutical compound of the present invention can be administered alone, but may be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; other proteins and peptides; synthetic polymers; microspheres; nanoparticles; and the like.

The formulations or pharmaceutical composition of the present invention may also be included, or packaged, with other non-toxic compounds, such as pharmaceutically acceptable carriers, excipients, binders and fillers including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Specifically, the pharmaceutically acceptable carriers, excipients, binders, and fillers contemplated for use in the practice of the present invention are those which render the compounds of the invention amenable to intravitreal delivery, intraocular delivery, ocular delivery, subretinal delivery, intrathecal delivery, intravenous delivery, subcutaneous delivery, transcutaneous delivery, intracutaneous delivery, intracranial delivery, topical delivery and the like. Moreover, the packaging material may be biologically inert or lack bioactivity, such as plastic polymers, silicone, etc. And may be processed internally by the subject without affecting the effectiveness of the composition/formulation packaged and/or delivered therewith.

The phrase "therapeutically effective amount" as applied to the formulations and compositions described herein, means the amount necessary to render the desired therapeutic result. For example, an effective amount is a level effective to treat, cure, or alleviate the symptoms of a disorder for which the therapeutic compound, biologic or composition is being administered. Amounts effective for the particular therapeutic goal sought will depend upon a variety of factors including the disorder being treated and its severity and/or stage of development/progression; the bioavailability, and activity of the specific compound or formulation used; the route or method of administration and introduction site on the subject; the rate of clearance of the specific compound or biologic and other pharmacokinetic properties; the duration of treatment; inoculation regimen; drugs used in combination or coincident with the specific composition or formulation; the age, body weight, sex, diet, physiology and general health of the subject being treated; and like factors well known to one of skill in the relevant scientific art. Some variation in dosage will necessarily occur depending upon the condition of the patient being treated, and the physician or other individual administering treatment will, in any event, determine the appropriate dose for an individual patient.

As used herein, "disorder" refers to a disorder, disease or condition, or other departure from healthy or normal biological activity, and the terms can be used interchangeably. The terms refer to any condition that impairs normal function. The condition may be caused by sporadic or heritable genetic abnormalities. The condition may also be caused by non-genetic abnormalities. The condition may also be caused by injuries to a subject from environmental factors, such as, but not limited to, cutting, crushing, burning, piercing, stretching, shearing, injecting, or otherwise modifying a subject's cell(s), tissue(s), organ(s), system(s), or the like.

As used herein, "treatment" or "treating" refers to arresting or inhibiting, or attempting to arrest or inhibit, the progression of a disorder and/or causing, or attempting to cause, the reduction, suppression, regression, or remission of a disorder and/or a symptom thereof. As would be understood by those skilled in the art, various clinical and scientific methodologies and assays may be used to assess the development or progression of a disorder, and similarly, various clinical and scientific methodologies and assays may be used to assess the reduction, regression, or remission of a disorder or its symptoms.

As used herein, "prevention" or "preventing" refers to arresting or inhibiting, or attempting to arrest or inhibit, the initial onset or development of a disorder. The prevention of a disorder may occur before any clinical signs of the disorder being prevented are recognized.

In one embodiment, the disorder being treated, delayed, and/or prevented by the formulations and compositions of the present invention is a neurodegenerative disease, such as dementia or cognitive decline, which includes at least Alzheimer's disease ("AD").

The many contributing factors to AD, together with each individual's unique makeup, genetic and otherwise (Exhibit 5), create a mind-boggling number of combinations which the present multi-component formulation is uniquely qualified to counter. If one component does not work with a particular individual, another component may. The multiple synergies between the different components of the present formulation increase the opportunity for at least one such synergy to provide an effective treatment for a particular person, unlike conventional single component drugs, which fail to benefit one in three patients and make one in seven to eight worse. (Exhibit 6, Exhibit 5, Exhibit 30).

Different forms of the present inventive formulation can be calibrated in order to adapt both to different individuals and to the different needs of a single individual. Implementing this concept is complicated, and the necessary research is challenging. However, the present formulation need not counter every cause in every individual. Rather, by countering the necessary causes, the present formulation will restore the body and brain to their normal function. Then the body and brain themselves will correct the remaining deficiencies. No drug can possibly correct every single cause of AD, but the present formulation will maximize the possibility.

The end result of the present inventive formulation is to push back the threshold age of development of AD or cognitive decline, i.e., to delay or prevent the onset of AD until later in life, or alternatively, to eliminate AD or cognitive decline altogether for some people. The formulation is not expected to be a cure for advanced AD. AD has a lengthy, non-linear, accelerating, and degenerative prodromal time period with ample opportunity for preventive intervention. Approximately 95% of AD cases are sporadic late-onset. The inventive formulation should be combined with early detection of mild cognitive impairment (MCI) and cognitive impairment which is not dementia (CIND), conditions that may develop into AD, in order to maximize its effectiveness. MCI/CIND is a fluid, non-homogeneous, and unstable state, which is a critical time to intervene. The inventive formulation may be marketed to all people over 50 as a preventive measure, including those with no cognitive impairment. A 5-year delay of the onset of AD would yield spectacular results (Exhibit 7).

In the present inventive formulation, herbals will help with cerebral blood flow, exert antioxidant and anti-inflammatory effects, strengthen the immune system, protect neurons, and slow the decline of "vital energy" both in the body and in the brain (Exhibit 22).

Although the present inventive formulation is different and the guidance (Exhibit 60) is not directed towards AD, the guidance (Exhibit 60) represents an important step forward in the FDA's consideration of a multi-component formulation of the present invention. Limiting the number of components involved should simplify the approval process. The history of safety and long-term use of most of the components of the present formulation should satisfy the safety criterion. Efficacy should be the only issue, and the degree of success already enjoyed by each component increases the odds of success of the combination. A fallback position is to sell the inventive formulation as a dietary supplement, either before or in lieu of securing FDA approval. Assuming that all of the components will qualify as dietary ingredients, the advantage is that under current law dietary supplements do not require FDA approval for sale, only prior safety notification. This saves the time and expense of obtaining FDA approval, which is considerable. The disadvantage is that dietary supplements cannot claim to cure a disease, but rather can only make structure and function claims, for instance improving brain health. This means that a supplement will not be prescribed by a majority of physicians. The market for pharmaceutical drugs far exceeds the market for dietary supplements. Still, the market for a supplement can be accessed immediately and can be substantial, particularly when backed by an outstanding product. In addition, the benefits of a dietary supplement reach the public sooner than a pharmaceutical drug, and at a cheaper price. Marketing the present inventive formulation as a dietary supplement before securing FDA approval is also an opportunity to obtain further evidence of its safety and efficacy.

In addition to the safety and efficacy of the formulation, testing will be focused on maximizing the exogenous stimulation of endogenous neuroprotective proteins (Exhibit 18), mild stress-induced hormesis, inhibiting the production of reactive oxygen species, restoring homeostasis, and on examining the interrelationships and synergies between such neuroprotective proteins, the immune system, DNA (including SIRT1), epigenetics, cell senescence, neurogenesis, and neurodegeneration (Exhibit 73).

The present invention provides a multi-component formulation for the prevention, delay, and/or treatment of cognitive decline, including Alzheimer's disease, and/or other neurodegenerative diseases. In one embodiment, the formulation comprises dimethyl sulfoxide ("DMSO"), at least one energy source component, at least one herbal component, and at least one nutritional component. In some embodiments of the present invention, the dimethyl sulfoxide component comprises about 5% to about 20% by weight (w/w) of the total formulation. In at least one embodiment, the at least one nutritional component comprises about 50% to about 75% (w/w) of the total formulation. In at least one embodiment, the at least one energy source component comprises about 5% to about 20% (w/w) of the total formulation. In at least one embodiment, the at least one herbal component comprises about 10% to about 20% (w/w) of the total formulation.

In one alternate embodiment, the present invention provides a formulation for the prevention, delay, and/or treatment of cognitive decline, including Alzheimer's disease, and/or other neurodegenerative diseases comprising methylsulfonylmethane ("MSM"), at least one energy source component, at least one of an herbal component or a nutritional component. Methylsulfonylmethane is a metabolite of DMSO, and approximately 15 percent of DMSO is converted to MSM in the body. It is noted that both DMSO and MSM occur naturally in small amounts in the human body.

In at least one embodiment, the at least one energy source component of the formulation of the present invention comprises fructose-6-phosphate. In some embodiments, fructose-6-phosphate comprises D-fructuose 6-phosphate disodium. In other embodiments, the at least one energy source component comprises fructose 1,6-disphosphate. In other embodiments, the at least one energy source component comprises glyceraldehyde-3-phosphate. In yet another embodiment, the at least one energy source component comprises a combination of fructose-6-phosphate, glyceraldehyde-3-phosphate, and fructose 1,6-disphosphate.

In at least one embodiment, the at least one herbal component comprises cinnamon. In some embodiments, cinnamon comprises *Cinnamomum burmannii*, and in at least one further embodiment, cinnamon is provided in the form of cinnamon extract. In some embodiments, the at least one herbal component comprises *Ningxia gougizi*. *Ningxia gouqizi* may comprise *Lycium barbarum* polysaccharide. In other embodiments, the nutritional component comprises wolfberry. Wolfberry may comprise *Lycium barbarum* polysaccharide. In other embodiments, the at least one herbal component comprises curcumin. In some embodiments, curcumin comprises turmeric extract from *Curcuma longa*. In another embodiment, the at least one herbal component comprises a combination of wolfberry or *Ningxia gouqizi*, cinnamon, and curcumin. In yet another embodiment, the at least one herbal component comprises cinnamon, wolfberry, *Ningxia gouqizi*, curcumin, ginkgo biloga, ginger, *ginseng*, garlic, or combinations thereof.

In at least one embodiment, the at least one nutritional component of the formulation of the present invention comprises an omega-3 fatty acid. In some embodiments, the omega-3 fatty acid comprises docosahexaenoic acid. In other embodiments, the omega-3 fatty acid comprises vegetable oil from microalgae. Vegetable oil from microalgae may further comprise docosahexaenoic acid. In a further embodiment, the omega-3 fatty acid comprises fish oil.

In at least one embodiment, the at least one nutritional component of the formulation of the present invention comprises resveratrol. In some embodiments, resveratrol comprises trans-resveratrol.

In some embodiments, the at least one nutritional component comprises blueberry. In some embodiments, blueberry comprises *Vaccinium virgatum*. In other embodiments, blueberry comprises *Vaccinium corymbosum*. Blueberry may be freeze dried blueberry powder. In some embodiments, blueberry may be wild blueberry and in other embodiments blueberry may be cultivated blueberry. In yet another embodiment, the at least one nutritional component comprises a combination of components selected from the group consisting of omega-3 fatty acid, resveratrol, blueberry, acai, pomegranate juice, alph-lipoic acid, oxyresveratrol, folic acid, apple juice, peach extract, walnut extract, caffeine, quercetin, grape juice, grape extract, epigallocatechin-3-gallate, watermelon juice, vitamin A, vitamin C, vitamin E, vitamin D, coenzyme Q10, and combinations thereof.

In at least one embodiment, *Ningxia gouqizi* or wolfberry comprises about 0.1% to about 1% (w/w) of the total formulation. In at least one embodiment, curcumin comprises about 1% to about 10% (w/w) of the total formulation. In at least one embodiment, cinnamon comprises about 5% to about 20% (w/w) of the total formulation. In at least one embodiment, omega-3 fatty acid, such as, but not limited to, docosahexaenoic acid, comprises about 10% to about 40% (w/w) of the total formulation. In at least one embodiment, resveratrol comprises about 5% to about 20% (w/w) of the total formulation. In at least one embodiment, blueberry comprises about 10% to about 40% (w/w) of the total formulation.

In at least one embodiment of the present invention, a multi-component formulation for the prevention and treatment of Alzheimer's disease is provided. More in particular, one embodiment of a multi-component formulation for the prevention and treatment of Alzheimer's disease comprises dimethyl sulfoxide, at least one energy source component, wolfberry or *Ningxia gouqizi*, curcumin, cinnamon, an omega-3 fatty acid, resveratrol, and blueberry. In one further embodiment, the omega-3 fatty acid comprises docosahexaenoic acid. In yet another embodiment, the at least one energy source component is selected from the group consisting of fructose-6-phosphate, glyceraldehyde-3-phosphate, fructose 1,6-disphosphate, and combinations thereof.

In at least one further embodiment of the present invention, a pharmaceutical composition for the prevention and treatment of Alzheimer's disease is provided. Specifically, one embodiment of a pharmaceutical composition comprises about 5% to about 20% (w/w) dimethyl sulfoxide, about 5% to about 20% (w/w) of at least one energy source component, about 10% to about 20% (w/w) of at least one herbal component, and about 50% to about 75% (w/w) of at least one nutritional component. In at least one embodiment, a pharmaceutical composition is in an oral dosage form.

A primary advantage of the present multi-component formulation is that it combines different components from different sources that persons skilled in the art would not seek to combine. Most of the components have a history of safety and efficacy with people, whose brain function differs from animals (Exhibit 61, Exhibit 69), along with the natural ability to cross the blood brain barrier without risky alteration and harmful side effects (Exhibit 62, Exhibit 56). In addition to decreasing the costs of development and regulatory approval, putting together existing components with higher degrees of success increases the probability of success for the combination. The combination's potential is further augmented by its focus on inducing neuroprotective proteins, mild stress-induced hormesis, inhibiting the production of reactive oxygen species, and restoring homeostasis, in order to enlist the brain's own defense mechanisms.

The failure of current AD drugs suggests the inapplicability of the reductionist model. Combinatorial chemistry, using computers to review all possible molecules and molecular targets, has not worked with AD. The present formulation combines targets and the remedies, which already work, make sense, and help the body and brain defend themselves.

Unlike conventional single component drugs, which have only one target, the present formulation can stimulate any number of additional inherent defenses in the brain in order to counter one or more of a plurality of contributing factors, such as exogenous stimulation of endogenous neuroprotective proteins, including but not limited to nicotinamide mononucleotide adenylyl transferase ("NMNAT"), synucleins, heat shock proteins, crystallins, and other neuronal molecular chaperones. As previously indicated, these proteins repair protein misfolding and boost immunity.

There is some movement in the scientific community towards a multifactorial approach. This means that the time is right for the best multifactorial approach, which will be more readily accepted than a totally new concept. Medical research also seems to suggest that remedies which help one brain disorder may help with other brain disorders, which opens up possible offshoots for the present formulation with brain injury, stroke, autism, Parkinson's disease, and spinal cord injury. Because of its multifactorial and holistic approach, the present formulation is uniquely positioned to work in conjunction with neurogenesis or other stem cell procedures and personalized medicine, and may even help with non-CNS disorders, such as heart disease. Medical research continues to find evidence of brain plasticity, even late in life. The brain can change, and the present formulation can be one instrument of that change.

Without further elaboration, it is believed that one skilled in the art can utilize the present invention to its fullest extent based on the disclosure herein. The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By citation of various references in this document, Applicant does not admit any particular reference is "prior art" to their invention.

EXAMPLES

The methods and formulations described herein are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicant does not seek to be bound by the theory presented.

Example I

The following material and methods are used for all the methods and compositions of EXAMPLE I.

Experimental Test Formulation and Dosage: A test formulation consists of 250 mg resveratrol (RESVIDA™, DSM Nutritional Products, France), 70 mg curcumin, as turmeric extract (BIO-CURCUM®, Arjuna Natural Extracts LTD, India), 10 mg *Ningxia gouqizi* extract (HongPharm Limited, Hong Kong), 500 mg wild blueberry powder (Allen's Blueberry Freezer, Inc., Ellsworth, Me.), 250 mg cinnamon extract (CINNULIN PF®, Integrity, Spring Hill, Tenn.), 500 mg docosahexaenoic acid ("DHA"), as docosahexaenoic acid single-cell oil (DHASC®, Martek Biosciences Corp., Columbia, Md.), 250 mg 99.98% dimethyl sulfoxide ("DMSO") (Jacob Laboratories, Portland, Oreg.), and 170 mg D-fructose-6-phosphate disodium ("F6P") (Sigma-Aldrich Handels GmbH). A daily dosage of the test formulation, based on the weight of the test subject, comprises 250 mg/kg resveratrol, 70 mg/kg curcumin, 10 mg/kg *Ningxia gouqizi*, 500 mg/kg blueberry, 250 mg/kg cinnamon, 500 mg/kg DHA, 250 mg/kg DMSO, and 170 mg/kg F6P.

Transgenic Animals: Test are conducted on female transgenic mice with the Swedish and the London mutations over-expressing human amyloid precursor protein (hAPP (751)) ($APP_{SL}$) under the control of the murine Thy-1 promoter with a C57BL/6xDBA background were utilized. The mice are tested in two groups, a placebo group (no test formulation) (n=18) and an experimental group (with the test formulation) (n=18). The mice utilized are at 6 months of age (±2 weeks) at the start of the study.

Delivery Of Experimental Test Formulation To Test Animals: Standard rodent chow (SSNIFF® R/M, 10 mm) and normal tap water are utilized to deliver the test formulation to the transgenic animals daily. The components of the formulation delivered via rodent chow are resveratrol, curcumin, *Ningxia gouqizi*, blueberry, cinnamon and DHA. The components of the formulation delivered via normal tap water are DMSO and F6P. In the placebo group, normal rat chow and tap water are utilized, minus the formulation components.

Timeframe Of Study: The study is performed for 6 months, wherein the test animals receive either a daily dosages of the test formulation, or the placebo, after which, behavioral and further analyses performed.

Morris Water Maze Behavioral Analysis: The Morris water maze ("MWM") test is a spatial navigation test to evaluate learning and memory. Training in the MWM takes place at the end of the treatment. The MWM consists of a white circular pool of a diameter of 100 cm, filled with tap water at a temperature of 21±2° C. The pool is virtually divided into four sectors. A transparent platform (8 cm diameter) is placed about 0.5 cm beneath the water surface. During all test sessions, except the pretest, the platform is located in the southwest quadrant of the pool.

Each mouse must perform three trials on each of four consecutive days. A single trial lasts for a maximum of one minute. During this time, the mouse has the chance to find the hidden, diaphanous target. After each trial mice are allowed to rest on the platform for 10-15 sec to orientate in the surrounding.

At least, one hour after the last trial on day 4, mice have to fulfill a so-called probe trial. During the probe trial, the platform is removed from the pool and the number of crossings over the former target position is recorded together with the abidance in this quadrant.

For the quantification of escape latency (the time [in seconds] the mouse needs to find the hidden platform and to escape from the water), of pathway (the length of the trajectory [in meters] to reach the target) and of the abidance in the goal quadrant in the probe trial, a computerized tracking system is used. All animals have to perform a visual test after the probe trial on the last day to exclude influence of impaired visual abilities on behavioral results.

Contextual Fear Conditioning Of Mice: Fear conditioning is conducted in an automated box (TSE-Systems, Germany). Mice are trained and tested on 2 consecutive days. On the training day, 10 minutes after treatment, mice receive a footshock (0.5 mA, 2 s) 5 seconds after being placed into the conditioning chamber. After 30 seconds, the mice are returned to their original cage.

Twenty-four hours after training, mice are tested by being returned to the conditioning chamber for 5 minutes without any shock, and the freezing behaviour is recorded by the automated system and evaluated separately every minute. Freezing is defined as a lack of movement, except for movement that is required for respiration.

Tissue Sampling: After 6 months of treatment and finishing all behavioural tasks, animals are sacrificed and blood, cerebrospinal fluid ("CSF"), and brains collected. CSF is obtained by blunt dissection and exposure of the foramen magnum. Upon exposure, a Pasteur pipette is inserted to the approximate depth of 0.3-1 mm into the foramen magnum. CSF is collected by suction and capillary action until flow fully ceased. Samples are immediately frozen on dry ice and stored at −80° C. until used for Aβ determination.

After CSF sampling, each mouse is placed in the dorsal position, the thorax is opened and a 26-gauge needle attached to a 1 cc syringe inserted into the right cardiac ventricular chamber. Blood is then collected into ethylenediaminetetraacetic acid ("EDTA") coated vials and consequently used to obtain plasma. To get plasma, blood samples from each mouse (in EDTA coated vials) is centrifuged (1000×g, 10 minutes, room temperature). Plasma (supernatant) is frozen in aliquots until used for Aβ determination.

Following blood sampling, mice are transcardially perfused with physiological (0.9%) saline. Thereafter, brains removed, cerebellum cut off and frozen, and hemispheres divided. The left hemisphere is used for biochemical analysis; the right hemisphere is fixed and used for histological investigations.

Brain Protein Extraction: After dividing the brain hemispheres of each mouse, the left hemisphere sample without the cerebellum is homogenized and separated into 4 fractions: TBS, Triton X-100, SDS, and FA.

After thawing, the hemispheres are homogenized with a Homogenizer "Ultra Turrax T8" at highest speed in TBS (20 mM Tris, 137 mM NaCl, pH=7.6; containing protease inhibitor cocktail; 100 mg brain wet weight per mL TBS). One aliquot (1 mL) is centrifuged (74,200×g for 1 h at 4° C.) and the supernatants stored at −20° C. (TBS fraction). The pellets are suspended in 1 mL Triton X-100 (1% in TBS), centrifuged as above, and the supernatants kept at −20° C. (Triton X-100 fraction). The pellets are suspended in 1 mL SDS (2% SDS in aqua bidest), centrifuged as above, and the supernatants kept at −20° C. (SDS fraction). The pellets out of the SDS fraction are suspended in 0.5 mL formic acid (70% in aqua bidest) prior to subsequent centrifugation (as above). The supernatants are neutralized with 9.5 mL TRIS (1M in aqua bidest.) and kept at −20° C. (FA fraction). All four fractions are used for Aβ38, Aβ40 and Aβ42 determination.

It can be assumed that TBS and Triton X-100 solubilize monomeric to oligomeric structures. Polymers like protofibrils and water insoluble fibrils can be resolved in SDS and FA. The investigation of all four fractions provides data also about the Aβ polymerization status.

Aβ Level Determination: Aβ38, Aβ40 and Aβ42 levels are measured in the four different brain homogenate fractions (TBS, Triton X-100, SDS and FA) and in CSF of each transgenic mouse with a commercially available Aβ-kit (Mesoscale Discovery). Samples from the brain preparations are analyzed in duplicate. Due to the small amount, CSF samples are analyzed only once. Aβ levels are evaluated in comparison to peptide standards as nanogram Aβ per gram brain or nanogram Aβ per mL CSF.

Tissue Fixation, Preparation And Sectioning: The right hemispheres of the mice are fixed by immersion in a freshly produced 4% solution of paraformaldehyde/PBS (pH 7.4) for one hour at room temperature. Thereafter, brains are transferred to a 15% sucrose PBS solution for 24 hours to ensure cryoprotection. The following day, brains are frozen in isopentane and stored at −80° C. until used for histological analysis.

The immersion-fixed and cryprotected frozen right hemispheres are used to prepare sagittal cryosections (10 μm thickness) for histological analysis on a Leica CM 3050S cryotome. Collection of sections starts at a level approximately 0.24 mm lateral from midline and extends through the hemisphere, usually resulting in collecting sections from 12 medio-lateral levels in order to cover the entire cortex and hippocampus. Sections are stored at −20° C. until used in immunohistochemistry (IHC).

Systematic random sets of sections (5 slices from 5 levels) are histologically investigated for 6E10 and ThioflavinS labeling, CD11b/GFAP and AT180 IHC using multi-channel fluorescence.

Determination Of Plaque Load: Plaque load is quantified by staining with 6E10 IHC directed against AA1-16 of the human amyloid peptide and ThioflavinS staining against beta-sheet structures in a double incubation. Region areas (hippocampus and cortex) are measured and plaque surface area and number of plaques per region area measured and counted using automated image analysis software (Image ProPlus, version 6.2).

Determination Of Inflammation: Astrocytes are evaluated using a rabbit anti-Glial Fibrillary Acidic Protein (DAKO®) antibody. Microglia is detected by a mouse anti-murine CD11b (SEROTEC®) antibody. Region areas (hippocampus and cortex) are measured and the percentage of GFAP (astrocytes) and CD11b immunoreactivity area (microglia) per region area are measured and counted using automated image analysis software (Image ProPlus, version 6.2).

Determination Of Phosphorylated Tau: Tau phosphorylation (pTau) around plaques is visualized immunohistochemically using an AT180 antibody. Clone AT180 recognizes PHF-Tau double-phosphorylated at Thr231 and Ser235.

Additional Evaluations: All remaining tissues from the mice are stored and used for later determination of neuroprotective proteins and epigenetic factors that might also play a role in AD. Statistical Analyses: Descriptive statistical analysis is performed on all measured parameters. Data is represented as mean±standard deviation (SD) or standard error of mean (SEM). In case of differences between groups, appropriate basic statistical tests (one-way ANOVA, T-test, etc.) are performed.

Example II

Further tests were conducted to assess the neuroprotective effects of a number of the components previously disclosed herein at various concentrations on primary chicken neurons, individually and in select combinations. The study components were applied to test specimens obtained on embryonic day 8 in vitro ("DIV8") for a period of forty-eight hours, after which, the test specimens were evaluated in accordance with MTT assay to determine cell viability.

Preparation of Test Specimens:

One day old fertilized eggs were stored under appropriate conditions until the start of breeding. On embryonic day zero, eggs were transferred to a breeding incubator and maintained under turning at 37.8° C. and 55% humidity until embryonic day eight.

All cell culture experiments were carried out under sterile conditions and all procedures were performed in a cell culture unit with special cell culture equipment. Glassware, forceps ad/or scissors were sterilized prior to experiments. Stock chemical solutions were obtained sterile, and final solution and culture medium were prepared fresh in a laminar airflow cabinet.

Neurons were prepared as follows. DIV8 embryos were transferred to plastic dish and decapitated. Bother hemispheres were removed, collected, and cleaned from any loose tissue. Hemispheres were then mechanically disassociated and $4.8 \times 10^4$ cells per well in a 96-well plate, and each well was seeded with 160 μL.

The cell culture medium for chicken telencephalon neurons consists of DMEM with 4.5 grams glucose, 5% Nu Serum, 0.01% gentamycin, and 2 mM L-glutamine. Cultures are maintained at 37° C., 95% humidity and 5% $CO_2$.

Test Procedure:

The study component(s) and vehicle controls ("VC") were applied to chicken neurons at DIV8 for forty-eight hours. The viability of the chicken neurons at DIV10 were determined according to an MTT cell viability assay.

MTT Cell Viability Assay: The viability of the chicken neurons were determined by MTT assay using a plate reader at 570 nanometers as described in SOP MET004. The assay measures the mitochondrial dehydrogenase activity which reduces yellow MTT to dark blue formazan crystals. As the reaction is catalyzed only in living cells, the assay is used to determine cell viability. MTT is added to each well at a concentration of 0.5 milligrams per milliliter. After two hours, the MTT containing medium is aspirated. Cells are lysed in 3% SDS and the formazan crystals are dissolved in isopropanol/hydrochloric acid. Optical density is measured with a plate-reader at a wavelength of 570 nanometers.

Cell survival rate is expressed as optical density, and values are calculated as a percentage of the vehicle control values, the vehicle control being 100%.

Test Results:

Part 1: Resveratrol (RESVIDA™, DSM Nutritional Products, France) showed positive effects on cell viability at concentrations of 20, 10 and 5 μM. Higher concentrations of 50 and 100 μM were toxic to cells.

Curcumin (BIO-CURCUMIN®, Arjuna Natural Extracts LTD, India) showed negative effects on cell viability at concentrations of 50, 20, 10 and 5 μM. The lowest concentration of 0.01 μM exhibited a positive influence on cell viability.

A toxic effect of cinnamon (CINNULIN PF®, Integrity, Spring Hill, Tenn.) was observed at a concentration of 1 and 0.1 mg/ml. Other concentrations of cinnamon did not influence cell viability compared to vehicle treated cells.

Dimethyl sulfoxide ("DMSO") showed toxic effects at 5%, all other concentrations tested exhibited a minor negative effect on cell viability compared to vehicle treated cells.

Methylsulfonylmethane ("MSM") induced only a minor negative effect at the highest concentration of 50 mM. All other applied concentrations showed no or even a slight increase in cell viability, seen at a concentration of 1 and 0.01 mM.

Docosahexaenoic acid ("DHA") (DHASCO®, Martek Biosciences Corp., Columbia, Md.) exhibited negative effects on cell viability at a concentration of 200 and 100 µM, whereas other applied concentrations had no significant influence.

Fructose 1,6-disphosphate ("FDP") induced toxic effects at the highest concentrations of 50, 10 and 5 mM. Other applied concentrations showed no significant effects.

Wolfberry, in the form of wolfberry extract, did not influence cell viability compared to vehicle treated cells, except at concentrations of 500 and 250 µg/ml which exhibited negative effects on cell viability.

Blueberry, in the form of blueberry extract, at concentrations of 500, 250 100 and 50 µg/ml induced toxic effects on cells, whereas 0.1 µg/ml even increased cell viability compared to vehicle treated cells.

Part 2: DMSO was analyzed at 0.1, 0.01, 0.001, 0.0001, and 0.00001% alone or in comparison to DMSO plus FDP at concentrations of 1000, 100, 10, 1 and 0.1 µM. Cell viability was determined as a percentage of vehicle treated cells. In general, the combination of DMSO plus FDP increased cell viability compared to DMSO only treated cells, independent of the DMSO concentration. The best combined effects of DMSO and FDP were achieved when FDP was chosen at a concentration of 1 µM and DMSO at 0.0001%. Thus, this combination was used for further studies.

MSM was analyzed at 0.0001, 0.001, 0.01, 0.1 and 1 mM alone or in comparison to MSM plus FDP at concentrations of 1000, 100, 10, 1 and 0.1 µm. Cell viability was determined as a percentage of vehicle treated cells. In general, the combination of MSM plus FDP induced higher cell viability compared to MSM treatment alone. The best combined effects of MSM and FDP were achieved when FDP was chosen at a concentration of 1 µM and MSM at concentrations of 1 and 0.1 µM. Since the effects of the two MSM concentrations were similar, the lower one of 0.1 µM was chosen for further studies.

In general, cells tolerated MSM better than DMSO when applied alone. In the subsequent combinations, MSM was used 128 times less concentrated than DMSO, however, achieving the same effects on cell viability (DMSO=12.8 µM=0.0001% and MSM 0.0001 mM=0.1 µM).

Part 3: A combination of MSM/FDP plus resveratrol at a concentration of 10 and 20 µM induced a significant increase in cell viability compared to MSM/FDP treatment alone. However, this effect was independent of MSM/FDP.

A combination of DMSO/FDP plus resveratrol at a concentration of 10 and 20 µM induced a significant increase in cell viability compared to DMSO/FDP treatment alone. Resveratrol at a concentration of 20 µM showed even better effects on cell viability as compared to resveratrol (20 µM) plus DMSO/FDP.

Curcumin at a concentration of 1 and 10 nM significantly increased cell viability when applied in combination with MSM/FDP. Interestingly, curcumin exhibited protective effects only in combinations with MSM/FDP but not when applied alone.

Curcumin at a concentration of 1 nM in combination with DMSO/FDP significantly increased cell viability. Only curcumin at a concentration of 1 nM in combination with DMSO/FDP showed better results on cell viability as curcumin alone at the same concentration.

A combination of MSM/FDP plus cinnamon at 10 ng/ml showed an increase in cell viability compared to MSM/FDP treatment alone, however, not statistically significant. Cinnamon at 0.1 ng/ml induced higher cell viability than a combination of MSM/FDP plus cinnamon at the same concentration.

Cinnamon in combination with DMSO/FDP significantly increased cell viability compared to DMSO/FDP treatment. However, effects of cinnamon in combination with DMSO/FDP were as high as cinnamon treatment alone.

DHA increased cell viability when applied in combination with MSM/FDP as compared to MSM/FDP alone, however, only significant at a concentration of 1, 10, and 100 nM. A combination of DHA plus MSM/FDP induced higher cell viability at all concentrations tested as DHA alone.

DHA increased cell viability when applied in combination with DMSO/FDP as compared to DMSO/FDP alone, however, only significant at a concentration of 1, 10, and 100 nM. A combination of DHA plus DMSO/FDP induced higher cell viability at a concentration of 1 and 10 nM as DHA alone. However, these effects were more pronounced in combination with MSM/FDP.

Blueberry in combination with MSM/FDP showed significant effects on cell viability compared to MSM/FDP or blueberry alone. In general, blueberry and wolfberry in combinations with MSM/FDP or DMSO/FDP were as good or slightly better than blueberry and wolfberry alone.

Part 4: Different combinations of MSM/FDP and DMSO/FDP plus resveratrol, curcumin and DHA together were compared to MSM/FDP or DMSO/FDP treatment alone. However, none of the combinations significantly increased cell viability compared to MSM/FDP or DMSO/FDP treatment. Only the addition of blueberry to MSM/FDP plus resveratrol, curcumin and DHA together induced minor positive effects on cell viability.

FIGS. 1 through 15 present graphical representations of the results of the assessment of the neuroprotective effects on primary chicken neurons of methylsulfonylmethane, dimethyl sulfoxide, curcumin, blueberry, docosahexaenoic acid, resveratrol, and fructose 1,6-disphosphate, at various concentrations, individually and in select combinations.

More in particular, FIGS. 1 through 5 present the results obtained for each of curcumin, blueberry, docosahexaenoic acid, resveratrol, and fructose 1,6-disphosphate, respectively, at various concentrations.

Figure 6:
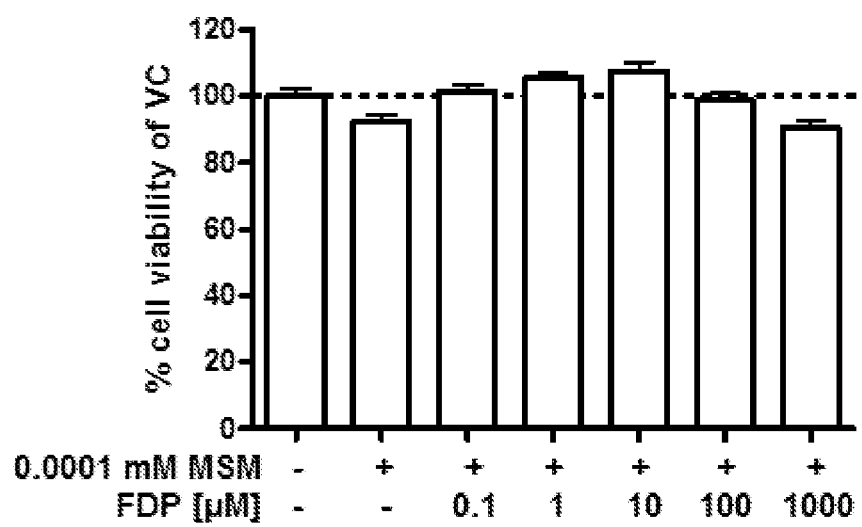
FIG. 6 is a graphical representation of the protective effects of methylsulfonylmethane alone and in combination with fructose 1,6-disphosphate at various concentrations on primary chicken neurons obtained in accordance with the testing protocols of Example II presented herein.
Figure 7:
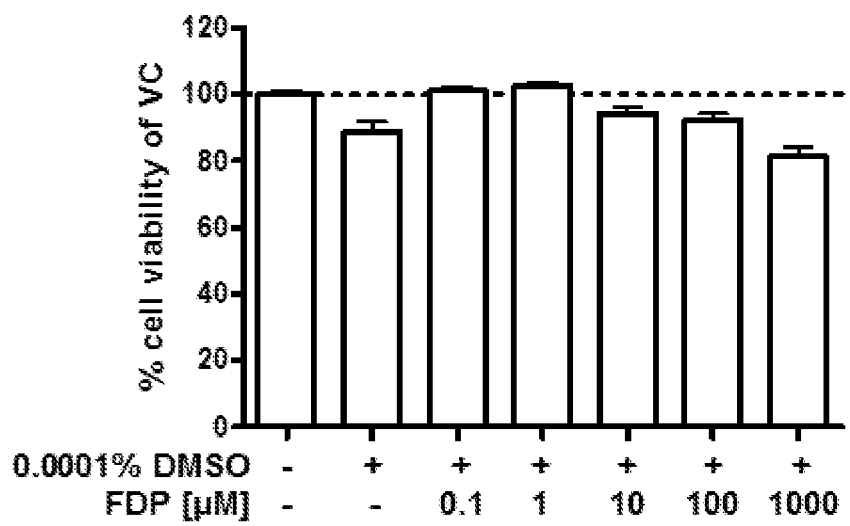
FIG. 7 is a graphical representation of the protective effects of dimethyl sulfoxide alone and in combination with fructose 1,6-disphosphate at various concentrations on primary chicken neurons obtained in accordance with the testing protocols of Example II presented herein.
Figure 8:
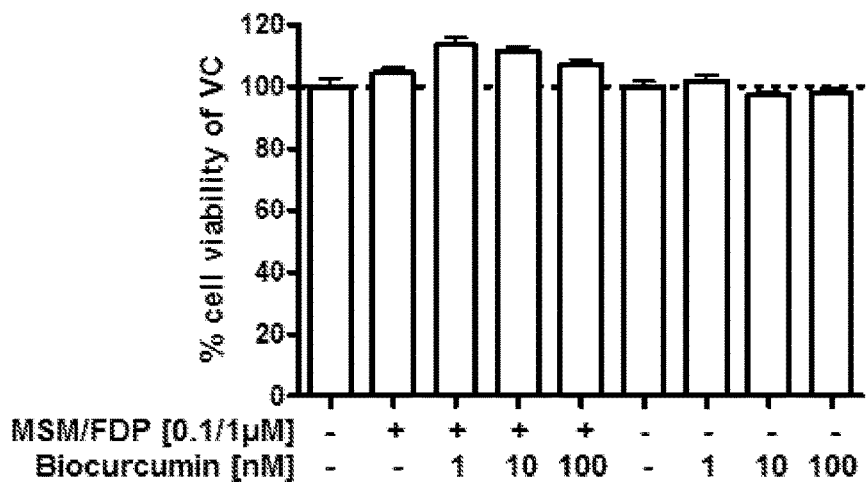
FIG. 8 is a graphical representation of the protective effects of methylsulfonylmethane and fructose 1,6-disphosphate in combination with curcumin at various concentrations on primary chicken neurons obtained in accordance with the testing protocols of Example II presented herein.
Figure 9:
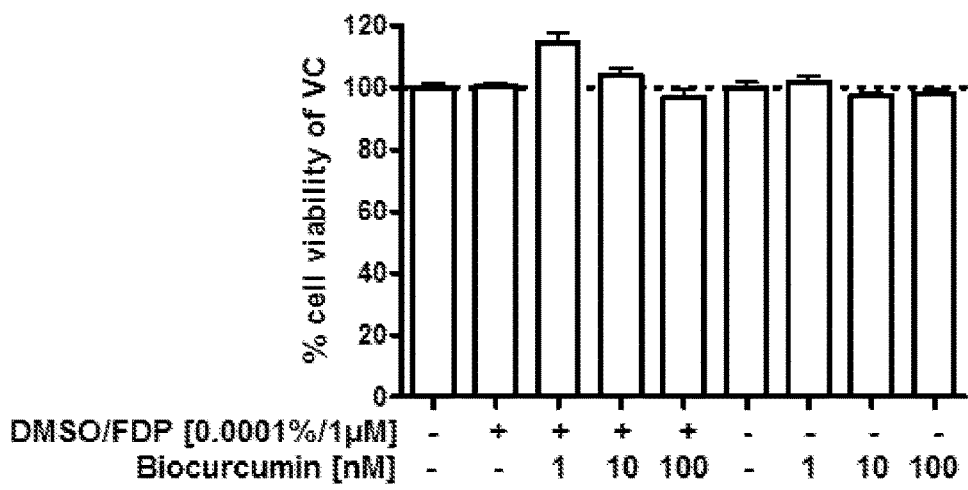
FIG. 9 is a graphical representation of the protective effects of dimethyl sulfoxide and fructose 1,6-disphosphate in combination with curcumin at various concentrations on primary chicken neurons obtained in accordance with the testing protocols of Example II presented herein.
Figure 10:
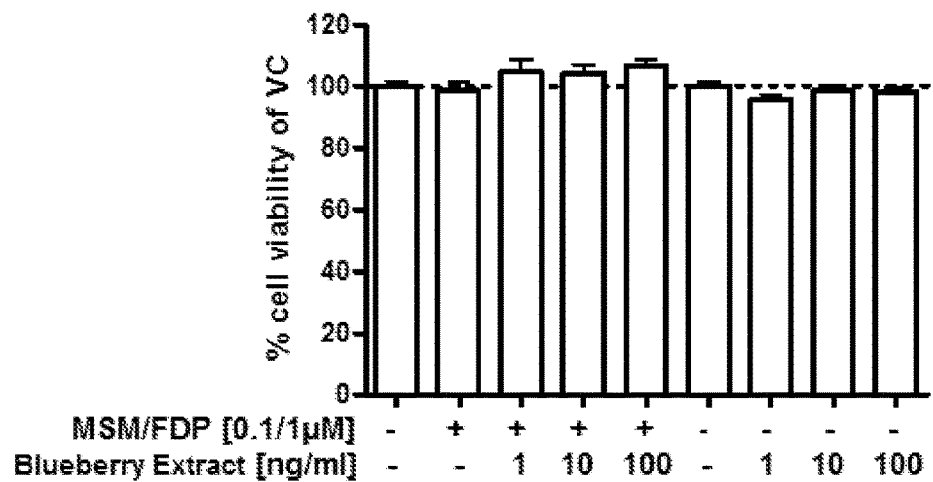
FIG. 10 is a graphical representation of the protective effects of methylsulfonylmethane and fructose 1,6-disphosphate in combination with blueberry extract at various concentrations on primary chicken neurons obtained in accordance with the testing protocols of Example II presented herein.
Figure 11:
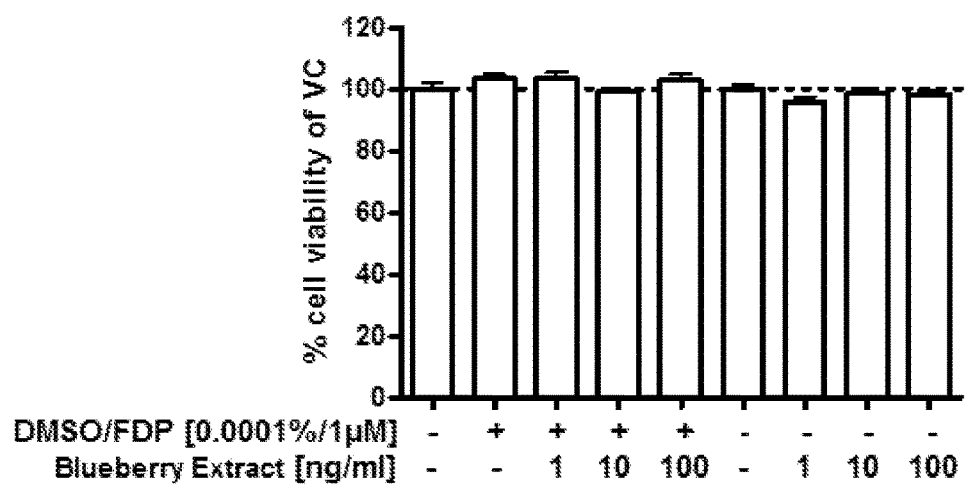
FIG. 11 is a graphical representation of the protective effects of dimethyl sulfoxide and fructose 1,6-disphosphate in combination with blueberry extract at various concentrations on primary chicken neurons obtained in accordance with the testing protocols of Example II presented herein.
Figure 12:
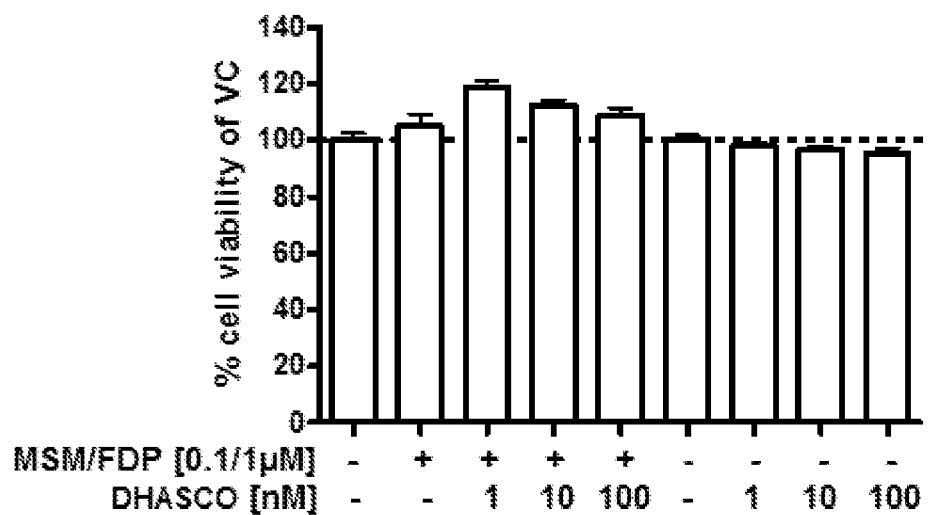
FIG. 12 is a graphical representation of the protective effects of methylsulfonylmethane and fructose 1,6-disphosphate in combination with docosahexaenoic acid at various concentrations on primary chicken neurons obtained in accordance with the testing protocols of Example II presented herein.
Figure 13:
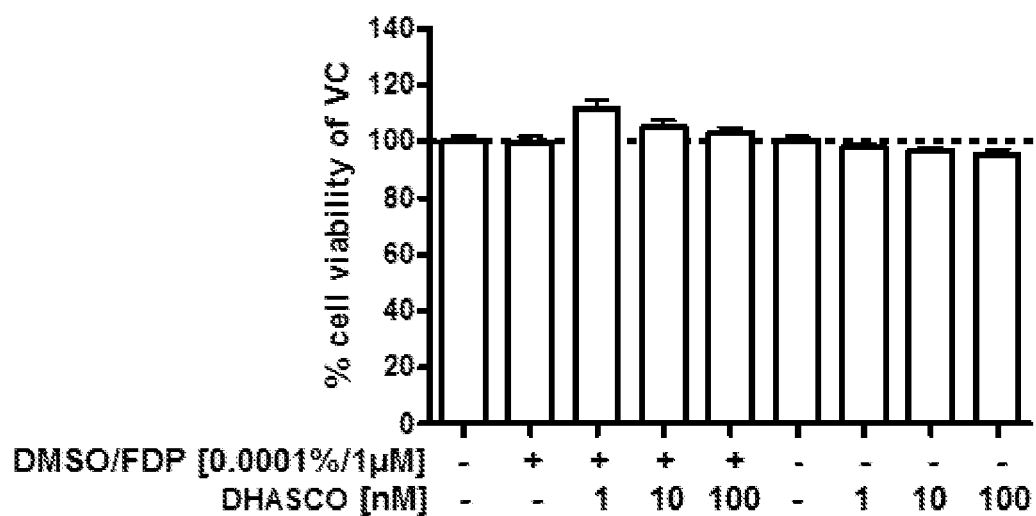
FIG. 13 is a graphical representation of the protective effects of dimethyl sulfoxide and fructose 1,6-disphosphate in combination with docosahexaenoic acid at various concentrations on primary chicken neurons obtained in accordance with the testing protocols of Example II presented herein.
Figure 14:
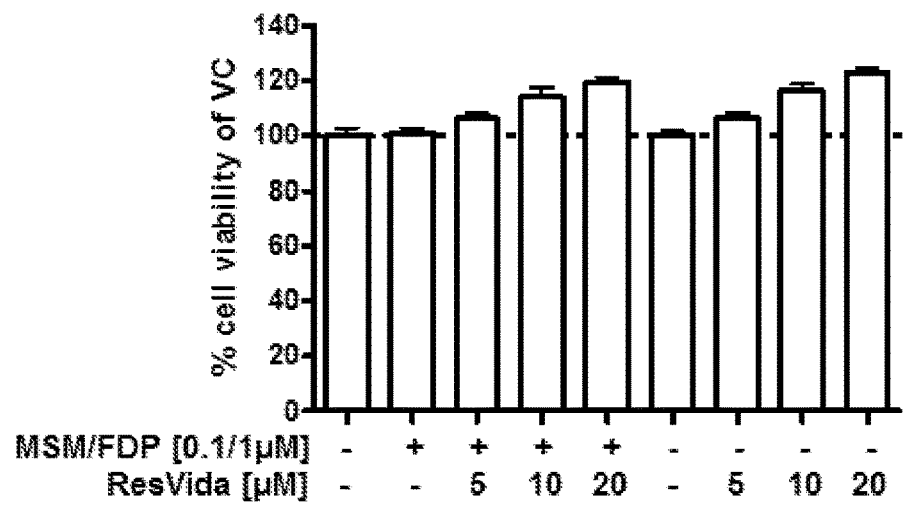
FIG. 14 is a graphical representation of the protective effects of methylsulfonylmethane and fructose 1,6-disphosphate in combination with resveratrol at various concentrations on primary chicken neurons obtained in accordance with the testing protocols of Example II presented herein.
Figure 15:
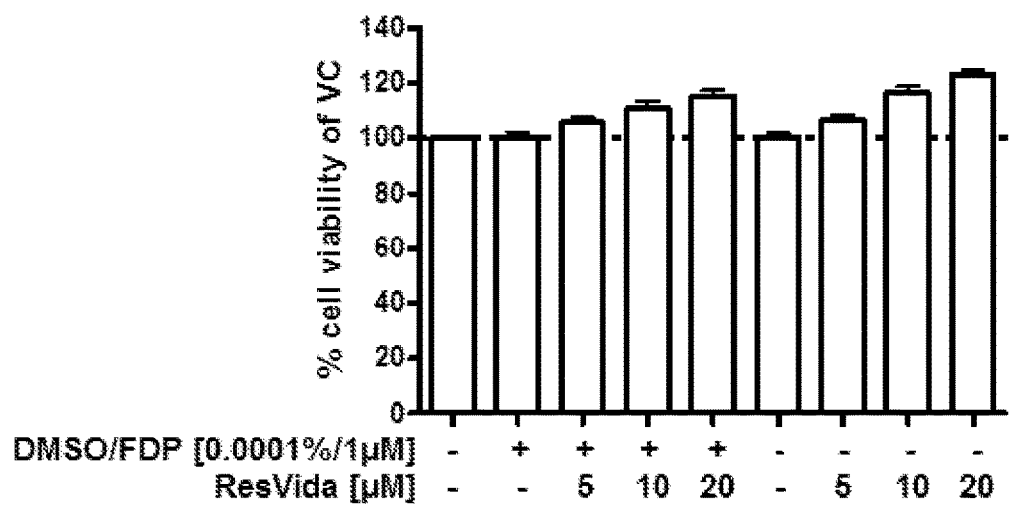
FIG. 15 is a graphical representation of the protective effects of dimethyl sulfoxide and fructose 1,6-disphosphate in combination with resveratrol at various concentrations on primary chicken neurons obtained in accordance with the testing protocols of Example II presented herein.

FIG. 6 presents the results obtained for methylsulfonylmethane both alone and in combination with fructose 1,6-disphosphate at various concentrations, and FIG. 7 presents the results obtained for dimethyl sulfoxide, also alone and in combination with fructose 1,6-disphosphate at various concentrations.

Finally, FIGS. 8, 10, 12, and 14 present the results obtained for methylsulfonylmethane and fructose 1,6-disphosphate in combination with various concentrations of curcumin, blueberry, docosahexaenoic acid, and resveratrol, respectively, while FIGS. 9, 11, 13, and 15 present the results obtained for dimethyl sulfoxide and fructose 1,6-disphosphate in combination with various concentrations of curcumin, blueberry, docosahexaenoic acid, and resveratrol, respectively.

The foregoing description of the specific embodiments fully reveals the general nature of the invention so that others can, by applying knowledge within the skill of the art, readily modify and/or adapt for various applications such specific embodiments, without undue experimentation, without departing from the general concept of the present invention. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Moreover, the breadth and scope of the present invention should not be limited by any of the above-described exemplary embodiments, but should similarly be defined only in accordance with the following claims and their equivalents.

REFERENCES

Exhibit 1:
Lee H, Casadesus G, Zhu X, Joseph J, Perry G, and Smith M: Perspectives on the Amyloid-B Cascade Hypothesis. Journal of Alzheimer's Disease 2004; 6: 137-145.
Whitehouse P and George D: Is Alzheimer's Disease an Outmoded Concept?-Putting the Patient and the Science First. International Conference on Alzheimer's Disease 2008, Poster P1-383.
Kwasi G. Mawuenyega, Sigurdson W, Ovod V, Munsell L, Kasten T, Morris J, Kevin E. Yarasheski, Bateman R: Decreased Clearance of CNS B-Amyloid in Alzheimer's disease. Science December 2010; 330:177.
Araman V, Sedeyn J, Dubay J, Vatsky S, Magele R: Essential or Toxic? The Two Faces of the Abeta 42 Peptide. International Conference on Alzheimer's Disease 2008, Poster P4-233.

Exhibit 2:
Luchsinger J, Ritz C, Patel B, Tang M, Mayeux R: Relation of Diabetes to Mild Cognitive Impairment. International Conference on Alzheimer's Disease 2006, Poster P3-129.
Cooper J: Biotin Deficiency and Sodium-Dependent Multi-Vitamin Transporter Dysregulation Triggers the Alzheimer's Cascade. International Conference on Alzheimer's Disease 2008, Poster P4-418.
Tucker K, Qiao N, Scott T, Rosenberg I, Spiro A: Homocysteine and Low B Vitamins Predict Cognitive Decline in Aging Men. American. Journal of Clinical Nutrition September 2005; 82(3), 627-635.
Lonneke M. de Lau, Refsum H, Smith D, Johnston C, Breteler M: Folate Levels and Cognitive Performance. International Conference on Alzheimer's Disease 2006, Poster P1-205.
Clarke R, Birks J, Nexo E, Emmens K, Schneede J, Ueland P, Scott J, Molloy A, Grimley-Evans J: Vitamin B-12, Holotranscobalamin and Risk of Cognitive Decline. International Conference on Alzheimer's Disease 2006, Poster P3-126.
Clare M, Evans D, Tang Ney C, Bienias J, Schneider J, Wilson R, Scherr P: Dietary Copper and High Saturated and Trans Fat Intakes Associated with Cognitive Decline. Archives of Neurology August 2006; 63:1083-1088.
Bates K and Martins R et al: Relationship between Cardiovascular Disease Risk Factors and Alzheimer's Disease AB Protein in Subjective Memory Complainers. International Conference on Alzheimer's Disease 2008, Poster P1-342.
Qiu C, Beng T. Winbla D, Fratiglioni L: Is Low Blood Pressure a Risk Factor for Dementia and Alzheimer's Disease in the Elderly? International Conference on Alzheimer's Disease 2006, Poster P1-232.
Caprini S, De Ronchi D, Atti R, Ujkaj M, Morri M, Dalmonte E, Karp A, Fratiglioni L: Mental Activity and Dementia Risk. International Conference on Alzheimer's Disease 2006, Poster P4-170
Gao S and Hendrie H. et al: Selenium and Cognitive Function in Rural Elderly Chinese. International Conference on Alzheimer's Disease 2006, Poster P3-124.
Kaufman Y, Anaki D, Freedman M: Cognitive Decline and Alzheimer's disease: Impact of Spirituality, Religiosity and Quality of Life. Neurology May 2007; 68 (18): 1509-1514.
Andrew M and Rockwood K: Social Vulnerability Predicts Cognitive Decline in a Prospective Cohort of Older Canadians. International Conference on Alzheimer's Disease 2006, Poster P3-127.
Ownby R, Crocco E, Acevedo A, John V, Loewenstein D. Depression and Risk for Alzheimer's disease. Archives of General Psychiatry May 2006; 63 (5): 530-538.
Guskiewicz K M, Marshall S W, Bailes J, McCrea M, Cantu R, Randolph C, Jordan B D: Association between Recurrent Concussion and Late-Life Cognitive Impairment in Retired Professional Football Players. Neurosurgery October 2005; 57 (4): 719-726.
Cullen K, Kocsi Z, Stone J: Microvascular Pathology in the Aging Human Brain: Evidence that Senile Plaques are Sites of Microhaemorrhages. Neurobiology of Aging 2006; 27: 1786-1796.
Jefferson A and Ruberg F et al.: Cardiac Function is Related to Maladaptive Brain Aging in Individuals with Mild Cognitive Impairment. International Conference on Alzheimer's Disease 2009, Poster.
Dai W, Lopez O, Carmichael O., Becker J, Kuller L, Gach H: Abnormal Regional Cerebral Blood Flow in Cognitively Normal Elderly Subjects with Hypertension. Stroke February 2008; 39: 1-6.
Weihong S, Sun X, Zhou W, Qing H, He G, Biel M. Hypoxia Facilitates Alzheimer's Disease Pathogenesis. International Conference of Alzheimer's Disease 2006, Poster P4-104.
Dede D and Ariogul S et al. Endothelial Dysfunction and Alzheimer's Disease. International Conference on Alzheimer's Disease 2006, Poster P4-105.
Aliev G, Palacios H, Walrafen B, Lipsitt A, Obrenovich M, Morales L: Brain Mitochondia as a Primary Target in the Development of Treatment Strategies for Alzheimer's disease. The International Journal of Biochemistry and Cell Biology 2009.
Kivipelto M and Nissinen A et al: Obesity and Vascular Risk Factors at Midlife and the Risk of Dementia and Alzheimer's Disease. Archives of Neurology October 2005; 62 (10):1556-1560.
Rusanen M, Kivipelto M, Quesenberry C, Zhou J, Whitmer R: Heavy Smoking in Midlife and Long-Term Risk of Alzheimer's Disease and Vascular Dementia. Archives of Internal Medicine February 2011; 171 (4):333-339.
Rocca W. Ovary Removal Surgery Elevates Risk for Dementia. Mayo Clinic Release Apr. 5, 2006.
Kiraly M and Kiraly S. Traumatic Brain Injury and Delayed Sequelae: TBI and Concussion are Precursors to Later-Onset Brain Disorders, including Early-Onset Dementia. Scientific World Journal November 2007; 7: 1768-176.

Exhibit 3:
Yuedes S and Csernansky J: Effects of Forced Versus Voluntary Exercise on Cognitive Deficits in TG. 2576 Mice. International Conference on Alzheimer's Disease 2006, Poster P1-047
Larson E, Wang L, Bowen J, McCormick W, Teri L, Crane P, Kukull W: Exercise is Associated with Reduced Risk for Incident Dementia Among Persons 65 Years of Age and Older. Annals of Internal Medicine January 2006; 144 (2):73-81.

Kraus W and Slentz C: Exercise Training, Lipid Regulation, and Insulin Action: A Tangled Web of Cause and Effect. Obesity (Silver Spring) December 2009; 17 (N3S): S21-S26.

Valdez G and Sanes J et al: Attenuation of Age Related Changes in Mouse Neuromuscular Synapses by Caloric Restriction and Exercise. Proceedings of the National Academy of Sciences August 2010; 17; 107 (33):14863-14868

Exhibit 4:

Lieberman D: Head to Toe Harvard Magazine. January-February 2011.

Wilson R, Schneider J, Boyle P, Arnold S, Tang Y, Bennett D: Chronic Distress and Incidence of Mild Cognitive Imperilment. Neurology June 2007; 68(24): 2085-2092.

McKinsey R and Fain S: Cerebral Perfusion in Alzheimer's Disease. International Conference of Alzheimer's Disease 2008, Poster P2-228.

Sowell R and Butterfield D: Assessing Immune-Related Oxidative Stress and Proteomics in Alzheimer's Disease. International Conference of Alzheimer's Disease 2008, Poster P4-177.

Ridley M: Connecting the Pieces of the Alzheimer's Puzzle. Wall Street Journal 2010.

Bialystok E and Freedman M: Delaying the Onset of Alzheimer's Disease: Bilingualism as a Form of Cognitive reserve. Neurology November 2010; 75(19):1726-1729.

Exhibit 5:

Hotz R: Tiny Gene Variations Can Even Alter Effect of the Pills We Take. Wall Street Journal Mar. 21, 2008.

Exhibit 6:

Plumridge H: Pharmaceutical Sector Remains Genetically Challenged. Wall Street Journal Jan. 20, 2011.

No Longer Treating Different Conditions Identically. Roche Nachrichten October 2008.

Personalized Healthcare. F. Hoffmann-La Roche A G. Website December, 2010

Porasad K and Andretta C et al: Multiple Antioxidants in the Prevention and Treatment of Neurodegenerative Disease: Analysis of Biologic Rationale. Current Opinion in Neurology December 1999; 12 (6): 761-770.

Grundman M, Grundman M, Delaney P: Antioxidant Strategies for Alzheimer's Disease. Proceedings of Nutrition Society May 2002; 61(2): 191-202.

Exhibit 7:

Impact of a 5-Year Delayed Onset of AD Due to a Treatment Breakthrough. Alzheimer's Association Website 2010.

de la Torre J C: Alzheimer's Disease is Incurable but Preventable. Journal of Alzheimer's Disease 2010.

Dartigues J: Prodromal Alzheimer's Disease. International Conference of Alzheimer's Disease 2009, Presentation S4-02-04.

Fackelmann K: 18% of All Boomers Expected to Develop Alzheimer's. USA Today Mar. 18, 2008.

Gabryelewicz T and Barcikowska M et al: Conversion to Dementia Over a Five Year Period among Patients with Mild Cognitive Impairment. International Conference of Alzheimer's Disease 2008, Poster P1-189.

Exhibit 8:

de la Torre J C: U.S. Pat. No. 5,516,526 Compositions Containing DMSO and Fructose 1, 6-Diphosphate May 14, 1996.

Exhibit 9:

Jacob S and de la Torre J C: Pharmacology of Dimethyl Sulfoxide in Cardiac and CNS Damage. Pharmacological Reports 2009; 61: 225-235.

Exhibit 10:

Regolin F and Winston G: Quantification of Total Oxidant Scavenging Capacity of Antioxidants for Peroxynitrite, Peroxyl Radicals, and Hydroxyl Radicals. Toxicology and Applied Pharmacology 1999; 156: 96-105.

Exhibit 11:

Camici G and Tanner F et al: Dimethyl Sulfoxide Inhibits Tissue Factor Expression, Thrombus Formation, and Vascular Smooth Muscle Cell Activation. Circulation 2006; 114: 1512-1521.

Exhibit 12:

Tatzelt J, Prusiner S, Welch W: Chemical Chaperones Interfere with the Formation of Scrapie Prion Protein. EMBO Journal December 1996; 15(23): 6363-6373.

Exhibit 13:

de la Torre J C, Nelson N, Sutherland R, Bappas B: Reversal of Ischemic-Induced Chronic Memory Dysfunction in Aging Rats with a Free Radical Scavenger-Glycolitic Intermediate Combination. Brain Research 1998; 779: 285-288.

Karaca M., Kilic E, Yazici B, Demir S, de la Torre J C: Ischemic Stroke in Elderly Patients Treated with a Free Radical Scavenger-Glycolytic Intermediate Solution: a Preliminary Pilot Trial. Neurological Research January 2002; 24 (1):73-80.

Bardutzky J, Meng X, Bouley J, Duong T, Ratan R, Fisher M: Effects of Intravenous Dimethyl Sulfoxide on Ischemia Evolution in a Rat Permanent Occlusion Model. Journal Cerebral Blood Flow Metabolism August 2005; 25 (8): 968-977.

Exhibit 14:

Kalt W and McCrae K et al: Effect of Blueberry Feeding on Plasma Lipids in Pigs. British Journal of Nutrition November 2007.

Exhibit 15:

Ebewe Pharma, Investigators' Brochure, Cerebrolysin in Dementia, May 2003.

Alvarez X and Moessler H: 24-Week, Double-Blind Placebo Controlled Study of Three Dosages of Cerebrolysin in Patients with Mild to Moderate Alzheimer's Disease. European Journal of Neurology January 2006; 13(1): 43-54.

Alvarez X and Cooke T et al: Neuropeptide Dietary Supplement N-PEP-12 Enhances Cognitive Function and Activates Brain Bioelectrical Activity in Healthy Elderly Subjects. Find Exp Clinical Pharmacology September 2005; 27 (7): 485-487.

Exhibit 16:

Brain Energizer: A Randomized, Double-Blind, Placebo-Controlled Trial, Changchung City 2nd Hospital, China 1997.

Exhibit 17:

Omar M, Chohan M, Li B, Boanchard J, Tung Y, Heaney A, Rabe A, Iqbal K, Iqbal L: Enhancement of Dentate Gyrus Neurogenesis, Dendritic and Synaptic Plasticity and Memory by Neurotrophic Peptide. Neurobiology of Aging August 2011; 22(8):1420-1434.

Egleton R and Davis T: Development of Neuropeptide Drugs that Cross the Blood Brain Barrier. NeuroRx January 2005; 2(1): 44-53.

Exhibit 18:

Yousuf O, Kitay B, Zhai R G: Dealing with Folded Proteins; Examining the Neuroprotective Role of Molecular Chaperones in Neurodegeneration. Molecules 2010; 15:6859-6887.

Zhai R G, Zhang F, Hiesinger P, Cao Y, Haueter C, Bellen H: NAD Synthase NMNAT Acts as a Chaperone to Protect against Neurodegeneration. Nature April 2008; 452: 887.

Chang R C and So K et al: Upregulation of Crystalins is involved in the neuroprotective effect of wolfberry on survival of retinal ganglion cells in rat ocular hypertension model. Journal of Cellular Biochemistry March 2010; 110:311-320.

Windisch M, Wolf H, Hutter-Paier B, Wronski R.: Role of Alpha-synuclein in Neurodegenerative Diseases: A Potential Target for New Treatments Strategies? Neurodegenerative Diseases 2008; 5: 218-221.

Blair L, and Dickey C et al: In Vivo Administration of Heat Shock Protein 27 Variants; Implications for tauopathies. Society for Neuroscience 2009 Poster 600.3.

Cavalucci V and Cecconi F: HSP 70 Deregulation in a Mouse Model of Alzheimer's Disease: A Potential mechanism for Early Synaptic Deficit. Society for Neuroscience 2009 Poster 317.6.

Wieten L and Broere F et al: HSP 70 Expression and Induction as a readout of detection of immune modulatory components in food. Cell Stress and Chaperones 2010; 15: 25-37.

O'leary J and Dickey C et al: Chemically Tuning Tau Fate Decisions with Chaperone Modulatoris. Society for Neuroscience 2009 Poster 600.2.

Ali Y and Zhai R G: NMNAT is a Stress Response Protein Regulated by the HFS/HIF1A Pathway. Journal of Biological Chemistry May 2011; 286(21):19089-19099.

Exhibit 19:
Aggarwal B et al: Curcumin-Biological and Medicinal Properties. Turmeric: Genus *Curcuma* 2007 Chapter 10.

Teitin M, Reuter S, Schmucker S, Dicato M, Diederich M: Induction of Heat Shock Response by Curcumin in Human Leukemia Cells. Cancer Letters July 2009; 279 (2):145-154.

Frautschy S and Cole M et al: Beta-Amyloid Oligomers Induced Phosphorylation of Tau and Inactivation of Insulin Receptor Substrate via C-Jun N-Terminal Kinase Signaling: Suppression by Omega 3 Fatty Acids and Curcumin. Journal of Neuroscience July, 2009; 29 (28): 9078-9089.

Saw C, Huang Y, Kong A: Synergistic Anti-Inflammatory Effects of Low Doses of Curcumin in Combination with Polyunsaturated Fatty Acids: DHA or EPA. Biochemical Pharmacology February 2010; 79 (3): 421-430.

Exhibit 20:
Napryeyemko O and Borzenko I: *Ginkgo Biloba* Special Extract in Dementia with Neuropsychriatic Features. Arzneimittelforschung 2007; 57(1): 4-11.

Exhibit 21:
Kim D, Kim J, Han Y: Alzheimer's Disease Drug Discovery from Herbs. Journal of Alternative and Complementary Medicine 2007; 13(3): 333-340.

Zhour Lin S, Yuan Q: Clinical Study on Effect of Shenyan Oral Liquid in Treating Mild Cognitive Impairment. Zhongguo September 2007; 27 (9): 793-795.

Li L, Zhang L, Zhao L, Wang W: Pharmacological Studies of Traditional Chinese Medicine to Treat Alzheimer's Disease. International Conference on Alzheimer's Disease 2006 Poster P4-273.

Exhibit 22:
Chang R C and Yuen T: Development of Gouqizi (*Lycium Barbarum*) as Neuroprotective Agents. The University of Hong Kong, August 2005.

Chang R C, Ho Y, Yu M, So K F: Medicinal and Nutraceutical uses of Wolfberry in Preventing Neurodegeneration in Alzheimer's Disease. Recent Advances on Nutrition and the Prevention of Alzheimer's Disease 2010: 169-185.

Ho Y, So K F, Chang R C: Anti-Aging Herbal Medicine-How and why can they be used in Aging Associated Neurodegenerative Diseases? Aging Research Reviews 2010; 9:354-362.

Chang R C and So K F: Use of Anti-Aging Herbal Medicine, *Lycium Barbarum*, against Aging Associated Diseases. What do we know so far? Cell Molecular Neurobiology August 2008; 28 (5):643-652.

Exhibit 23:
Qin W and Pasinetti G et al: Neuronal SIRT1 Activation as a Novel Mechanism Underlining the Prevention of Alzheimer's Disease Amyloid Neuropathology by Calorie Restriction. Journal of Biological Chemistry June 2006.

Morillo L and Jacob-Filho W et al: Obesity and Cognition in an Interdisciplinary Program to Treat Aged Women Obesity. International conference on Alzheimer's disease 2008 Poster P2-117.

Exhibit 24:
Lombardo N and Zhang X et al: Memory Preservation Diet for Reducing Risk and Slowing Progression of Alzheimer's Disease. International Conference on Alzheimer's disease 2006 Poster P-157.

Scarmeas N, Stern Y, Tang M, Mayeux R, Luchsinger J: Mediterranean Diet and Risk for Alzheimer's Disease. Annals of Neurology June 2006; 59(6): 912-921.

Laitenan M, Ngandu T, Helkala E, Nissenan A, Soininin H, Kivipelto M: Fat Intake at Midlife and Cognitive Impairment Later in Life. International Conference on Alzheimer's Disease 2006 Poster P3-125.

Exhibit 25:
Wolfe K, Kang X, He X, Dong M, Zhang Q, Liu R: Cellular Antioxidant Activity of Common Fruits. Journal of Agricultural and Food Chemistry July 2008.

Krikorian R and Joseph J et al: Blueberry Supplementation Improves Memory in Older Adults. Journal of Agricultural and Food Chemistry December 2009.

Spencer J: The Impact of Fruit Flavonoids on Memory and Cognition. British Journal of Nutrition July 2010; 104: S40-S47.

Malin D and Joseph J: Short-term Blueberry Enriched Diet Prevents and Reverses Object Recognition and Memory Loss in Aging Rats. Nutrition 2011; 27:338-342.

Exhibit 26:
Qin B, Panickar K S, Anderson R A. Cinnamon: Potential Role in the Prevention of Insulin Resistance, Metabolic Syndrome and Type 2 Diabetes. Journal diabetes science technology May 2010; 4(3): 685-693.

Anderson R A: Chromium and Polyphenols from Cinnamon Improve Insulin Sensitivity. Proceedings Nutrition Society February 2008; 67(1): 48-53.

Baker L and Craft S et al: Regional Overlap of Cerebral Glucose Metabolism at Risk and During List Learning for Older Insulin Resistant and Alzheimer Adults. International Conference on Alzheimer's Disease Poster P2-224.

Turner A, Fisk L, Nalivaeva N: Targeting Amyloid-Degrading Enzymes as Therapeutic Strategies in Neurodegeneration. Annals of the New York Academy of Sciences 2004; 1035: 1-20.

Exhibit 27:
Rodrigues R. and Almeida O et al: Total Oxidant Scavenging Capacity of Acai Seeds and Identification of their Polyphenol Compounds. Journal of Agricultural Food Chemistry June 2006; 54 (12): 4162-4167.
Exhibit 28:
Ignarro L, Byrns R, Sumi D, De Nigris F, Napoli C: Pomegranate Juice Protects Nitric Oxide against Oxidative Destruction and Enhances the Biological Actions of Nitric Oxide. Nitric Oxide September 2006; 15 (2): 93-102.
Hartman R and Holtzman D et al: Pomegranate Juice Decreases Amyloid Load and Improves Behavior in a Mouse Model of Alzheimer's Disease. Neurobiology diseases September 2006.
Exhibit 29:
Maczurek A and Munch G et al: Lipoic Acid as an Anti-Inflammatory and Neuroprotective Treatment for Alzheimer's Disease. Advance Drug Delivery Review July 2008.
Sharma M, Briyal S, Gupta Y: Effect of Alpha Lipoic Acid, Melatonin and Trans Resveratrol on Spatial Memory Deficit in Rats. Indian Journal of Physiology October 2005; 49(4): 395-402.
Exhibit 30:
Putics A, Vegh E, Csermery P, Soti C: Resveratrol Induces the Heat Shock Response and Protects Human Cells from Severe Heat Stress. Antioxidant Redox Signaling January 2008; 10(1): 65-75.
Ladiwala R and Tessier P: Resveratrol Selectively Remodels Soluble Oligomers and Fibrils of Amyloid Abeta into Off-Pathway Conformers. Journal Biological Chemistry July 2010; 285 (31): 24228-24237.
Kennedy D, Wightman E, Reay J, Lietz G, Okello E, Wilde A, Haskell C: Effects of Resveratrol on Cerebral Blood Flow Variables and Cognitive Performance in Humans. American Journal of Clinical Nutrition June 2010; (6): 1590-1597.
Baur J A and Sinclair D et al: Resveratrol Improves Health and Survival Of Mice On a High Calorie Diet. Nature November 2006.
Exhibit 31:
Chao J and Chang R C et al: Dietary Oxyresveratrol Prevents Parkiansonian Neurotoxicity. Free Radical Biology and Medicine 2008; 45: 1019-1026.
Exhibit 32:
Soffrizzi V and Panza F et al: Alcohol Consumption, Mild Cognitive Impairment and Progression to Dementia. Neurology May 2007; 68(21): 1790-1799.
Exhibit 33:
Das U: Folic Acid and Polyunsaturated Fatty Acids Improve Cognitive Function and Prevent Depression, Dementia, and Alzheimer's Disease—but how and why? Prostaglandins Leukot Essential Fatty Acids January 2008; 78(1): 11-19.
Exhibit 34:
Chan A, Graves V, Shea T: Apple Juice Concentrate Maintains Acetylcholine Levels following Dietary Compromise. Journal of Alzheimer's Disease August 2006; 9(3): 287-291.
Exhibit 35:
Suh S, Koo B, Jin U, Hwang J, Lee I, Kim C: Pharmacological characterization of orally active cholinesterase inhibitory activity of *Prunus Persica* L. Batsch in Rats. Journal of Molecular Neuroscience 2006; 29(2): 101-107.
Exhibit 36:
Shukitt-Hale B, Cheng V, Bielinski D, Joseph J: Walnuts can improve motor and cognitive function in aged rats. Society for Neuroscience 2007 poster 256.14.

Chauhan N, Wang K, Wegiel J, Malik M: Walnut extract inhibits the Fibrillization of Amyloid Beta-Protein and also Defibrillizes its Preformed Fibrils. Current Alzheimer Research August 2004; 1(3): 183-188.
Exhibit 37:
Cao C and Arendash G: Caffeine Synergizes with another Coffee Component to Increase Plasma GCSF; Linkage to Cognitive Benefits in Alzheimer's Mice. Journal of Alzheimer's Disease 2011; 25(2): 323-335.
Exhibit 38:
Frautschy S and Cole G: What was lost in translation in the DHA trial is whom you should Intend to Treat. Alzheimer's Research & Ttherapy January 2011; 3(1): 2.
Jicha G and Markesbery W: Omega-3 Fatty Acids: Potential Rule in the Management of Early Alzheimer's Disease. Clinical Interventions in Aging 2010; 5:45-61.
Yurko-Mauro K et al: Beneficial Effects of Docosahexanoic Acid on Cognition in Age-Related Cognitive Decline. Alzheimer's & Dementia 2010:1-9.
Eckert G, Franke C, Noeldner M, Mueller W: Plant Derived Omega-3 Fatty Acid Modulate Fatty Acid composition in the Brain and provide Neuroprotective Properties Society for Neuroscience 2008 Poster 340.19.
Muldlon M and Manuck S et al: Serum Phospholipid DHA is Associated with Cognitive Functioning during Middle Adulthood. Journal of Nutrition April 2010; 140(4):848-853.
Exhibit 39:
Heo H and Lee C: Protective Effects of Quercetin and vitamin C against oxidative stress induced Neurodegeneration. Journal Agricultural Food Chemistry December 2004; 52(25): 7514-7517.
Exhibit 40:
Ho L and Pasinetti G: Isolation and Characterization of Grape Derived Polyphenolic Extracts with Abeta-Lowering Activity that could be developed for Alzheimer's Disease. Society for Neuroscience 2007 Poster 548.7.
Exhibit 41:
Dragicevic N, Bradshaw P et al: Green Tea Epigallocatechin-3-Gallate and other Flavonoids Reduce Alzheimer's Amyloid Induced Mitochondrial Dysfunction. Journal of Alzheimer's Disease June 2011; 26(3).
Exhibit 42:
Collins J and Clevidence B et al: Watermelon Consumption Increases Plasma Arginine Concentrations in Adults. Nutrition March 2007; 23(3): 261-266.
Exhibit 43:
Tabet N, Mantle D, Walker Z, Orrell M: Endogenous Anti-Oxidant Activities in Relation to Concurrent Vitamins A, C, and E Intake in Dementia. International Psychogeriatrics March 2002; 14(1): 7-15.
Exhibit 44:
Richards J and Aviv A, et al: Higher Serum Vitamin D Concentrations are Associated with Longer Leukocyte Telomere Length in Women. American Journal of Clinical Nutrition November 2007; 86(5): 1420-1425.
Exhibit 45:
Yang X and Chang R C. et al: Coenzyme Q10 Attenuates Hyperphosphorylation of tau. International Conference on Alzheimer's Disease 2008 Poster P2-158.
Exhibit 46:
Kamphuis P, Scheltens P: Can Nutrients Prevent of Delay Onset of Alzheimer's Disease? Journal of Alzheimer's Disease 2010; 20:765-775.
Parachikova A et al: Formulation of a Medical Food Cocktail for Alzheimer's Disease. PLoS ONE November 2010; 5(11): e14015.

Beking K and Vieira A: Flavonoids and Alzheimer's Disease Prevention; An Ecological Analysis of Potential Neuropotective Factors. International Conference on Alzheimer's Disease 2009 Poster.

Chan A and Remington R et al: A Vitamin/Nutriceutical Formulation Improves Memory and Cognitive Performance in Community-Dwelling Adults without Dementia. Journal of Nutritional Health and Aging 2010; 14 (3) 224-230.

Tohda C, Naito R, Joyashiki E: Kihi-To, an Herbal Traditional Medicine, Improves Abeta-Induced Memory Impairment and Losses of Neurites and Synapses. BMC Complementary and Alternative Medicine August 2008; 8:49.

Exhibit 47:
Presley T and Miller G et al: Acute Effect of a High Nitrate Diet on Brain Perfusion in Older Adults, Nitric Oxide October 2010.

Exhibit 48:
de la Torre J C, Aliev G: Inhibition of Vascular Nitric Oxide after Rat Chronic Brain Hypoperfusion. Journal of Cerebral Blood Flow & Metabolism 2005; 25: 663-672.

Exhibit 49:
Bondy S and Sharman E et al: Retardation of Brain Aging by Chronic Treatment with Melatonin. Annals of New York Academy of sciences 2004; 1035: 197-215.

Exhibit 50:
Wu H and Zhang Y et al: Hematopoietic Effect of fractions from the enzyme-digested Colla Corii Asini on Mice with Anemia. American Journal of Chinese Medicine 2007; 35(5): 853-866.

Yao D, Zhang Y, Zhou Y: Effects of Colla Corii Asini on the Hemodynamics, Hemorheology and Microcirculation during Endotoxin Shock in Dogs. Zhongguo Zhong Yao Za Zhi January 1989; 14(1): 44-46, 64.

Exhibit 51:
Park S and Klessig D et al: Methyl Salicylate is a Critical Mobile Signal for Plant Systemic Acquired Resistance. Science October 2007; 318: 113-116.

Exhibit 52:
Singh C and Thompson R: Allopregnanolone Reverses the Learning and Memory Deficits of Adult Triple Transgenic Alzheimer's Disease Mice. Society for Neuroscience 2008 Poster 554.9.

Exhibit 53:
Myung C and Kang J et al: Improvement of Memory by Dieckol and Phlorofucofuroeckol in Ethanol-Treated Mice. Archives of Pharmaceutical Research June 2005; 28(6): 691-698.

Exhibit 54:
Voscular P, Brennan C, Chen J: Calpain Mediated Signaling Mechanisms in Neuronal Injury and Neurodegeneration. Molecular Neurobiology August 2008; 38(1): 78-100.

Exhibit 55:
Putis A and Soti C et al: Zinc Supplementation Boosts the Stress Response in the Elderly: HSP70 status is linked to Zinc Availability in peripheral lymphocytes. Exp Gerontology May 2008; 43(5):452-461.

Exhibit 56:
Hanson L and Frey W: Intranasal Delivery bypasses the Blood Brain Barrier to Target Therapeutic Agents to the Central Nervous System and Treat Nurodegenerative Disease. BMC Neuroscience December 2008; 9S3:S5.

Silva G: Nanotechnology Approaches to Crossing the Blood Brain Barrier an Drug Delivery to the CNS. BMC Neuroscience December 2008; 9S3:S4.

Patel D and Patel N: True Healing Art of Alzheimer's by Holistic Homeopathy. International Conference of Alzheimer's Disease 2006 Poster P1-448.

Mattson M and Cheng A: Neurohormetic Phytochemicals: Low Dose Toxins that Induce Adaptive Neuronal Stress Responses. Trends in Neuroscience September 2006; 29(11).

Lonsdorf N, Arenander A, Shah Y: Neurological Understanding of Ayurvedic Medicine and its Application to Dementia Prevention. International Conference on Alzheimer's Disease 2006 Poster P-168.

Goldsmith H: Treatment of Alzheimer's Disease by Transposition of the Omentum. Annals of New York Academy of Science 2002; 977: 456-467.

Du Y, Tian Q, Sun G, Wang J: Effect of Moxibustion on Spatial Memory of Aging Rats and the Underlying Mechanisms. International Conference on Alzheimer's Disease 2006 Poster P4-415.

Zoladz P, Raudenbush B: Cognitive Enhancement through Stimulation of the Chemical Senses. North American Journal of Psychology 2005; 7(1).

Neubauer R and Yutsis P: New Frontiers: Anti-Aging Properties of Hyperbaric Oxygen Therapy.

Ricard N, Toukhsati S, Field S: The Effect of Music on Cognitive Performance. Behavior Cognition Neuroscience Review December 2005; 4 (4) 235-261.

Bauer D et al: Photobiomodulation Attenuates CNS Oxidative Stress. Society for Neuroscience 2008 Poster 702.13.

Zelinski E et al: Randomized Controlled Trial of a Brain Plasticity-Based Training Program for Age Related Cognitive Decline. Society for Neuroscience Poster.

Herrera A S et al: Human Photosynthesis and its Impact on Alzheimer's and other Neurodegenerative Diseases. International Conference on Alzheimer's Disease 2008 Poster P-466.

Exhibit 57:
Jeong Y, Kim J, Lee K, Suh Y: Environmental Enrichment Compensates the Effects of Stress on the Disease Progression in the TG 2576 Mice an Alzheimer's Disease Model. Society for Neuroscience 2007 Poster 691.16.

Arendash G et al: Environmental Enrichment Sessions are Sufficient to Provide Cognitive Benefits to Impaired Alzheimer's Transgenic Mice without Affecting Brain or Plasma AB Levels. International Conference on Alzheimer's Disease 2008 Poster P1-068.

Exhibit 58:
Chen S: Regulatory Prospects of Botanical New Drugs. Medicine in the 21st Century Tri-Conference & Bio-Forum 2004, Shanghai, China.

Chen S, et al. New Therapies from Old Medicines. Nature Bio Technology October 2008; 26(10): 1077-1083.

Exhibit 59:
Xie P: Changing Mind to Match the Feature of TCM for Developing Chromatographic Fingerprint to Access the Quality of Herbal Medicine. Medicine in the 21st Century Tri-Conference & Bio-Forum 2004, Shanghai, China.

Exhibit 60:
US Food and Drug Administration. Guidance for Industry Codevelopment of Two or More Unmarketed Investigational Drugs for use in Combination. December 2010 Federal Register 75; 240: 78259.

Exhibit 61:
Mathews A: Recent Cases Point to the Limitations of Animal Drug Tests. Wall Street Journal Mar. 31, 2007.

Exhibit 62:

Banks W: Developing Drugs that can cross the Blood-Brain Barrier. Applications to Alzheimer's Disease BMC Neuroscience 2008; 9 (S3): S2.
Patel M et al: Getting into the Brain, Approaches to Enhance Brain Drug Delivery CNS Drugs 2009; 23(1):35-52.
Exhibit 63:
U.S. Provisional Patent Application No. 61/404,769, Filed on Oct. 12, 2010, now abandoned.
Exhibit 64:
Voelker R: Guideline: Dementia Drugs Benefits Uncertain. JAMA April 2008; 299(15):1763.
Neuroscience under Threat as Big Pharma Backs Off, Reuters News. Feb. 11, 2011 Press Release.
Shaywytz D and Taleb N: Drug Research Needs Serendipity, Financial Times 2010.
Zamiska N: Dueling Therapies: Is a Shotgun Better than a Silver Bullet. Wall Street Journal Mar. 2, 2007.
Newman D and Cragg G: Natural Products as Sources of New Drugs over the Last 25 Years. Journal Natural Products 2007; 70: 461-477.
Alzheimer's Disease to Quadruple Worldwide by 2050. Johns Hopkins School of Public Health Jun. 10, 2007.
Exhibit 65:
de la Torre J C: Vascular Risk Factor Detection and Control may Prevent Alzheimer's Disease. Aging Research Reviews 2010; 9:218-225.
de la Torre J C: Alzheimer's Disease as a Vascular Disorder. Stroke 2002; 33: 1152-1162.
Exhibit 66:
Chang R C et al: Significance of Molecular Signaling for Protein Translation Control in Neurodegenerative Diseases. Neurosignals 2007; 15(5):249-258.
Exhibit 67:
Randomized Double Blind, Placebo-Controlled Trial to Evaluate the Safety and Efficacy of New Therapy in Patients with Mild to Moderate Probable Alzheimer's Disease. JSW Life Sciences, Graz, Austria.
Exhibit 68:
Vellas B: Recommendations and Outcomes of Disease Modifying Drugs. International Conference on Alzheimer's Disease 2008 Presentation S2-04-01.
Siemers E: Disease Modification: Will We Know It When We See It? International Conference on Alzheimer's Disease 2008 Presentation S2-04-02.
Jones R, Schindler R et al: Variation in Placebo Decline across a Decade of Alzheimer's Disease Trials. International Conference on Alzheimer's Disease 2008 Poster.
Exhibit 69:
Rosen R F et al: Patterns of AB Accumulation in Alzheimer's and Aged Primate Brain. International Conference on Alzheimer's Disease 2006 Poster P2-005.
Rosen R F et al: Tauopathy with Paired Helical Filaments in an Aging Chimpanzee. Journal of Comparative Neurology May 2008; 509(3): 259-270.
Exhibit 70:
Barger S: Cooperative Ideas about Cooperative Strategies. Annals of New York Academy of Science 2004; 1035: 350-353.
Ramassamy C: Emerging Role Of Polyphenolic Compounds in the Treatment of Neurodegenerative Diseases: A Review of their Intracellular Targets. European Journal of Pharmacology 2006; 545:51-64.
Steel K: Alzheimer's Disease may not be a disease at all: BNJ Jun. 16, 2006.
Exhibit 71:
Curtis M and Eriksson P et al: Human Neuroblasts Migrate to the Olfactory Bulb via a Lateral Ventricular Extension. Science February, 2007.
Exhibit 72:
Park A: Alzheimer's Unlocked. Time Magazine Oct. 25, 2010.
Exhibit 73:
Passos J and Vonz G et al: Feedback between P21 and Reactive Oxygen Production Is Necessary for Cell Senescence. Molecular Systems of Biology February 2010; 6: 347.
Kad N, Wang H, Kennedy G, Warshaw D, Van Houten B: Collaborative Dynamic DNA Scanning by Nucleotide Excision Repair Proteins Investigated by Single-Molecule Imaging of Quantum-Dot-Labeled Proteins. Molecular Cell March 2010; 37(5): 702-713.
Reuter S, Gupta S, Park B, Goel A, Aggarwal B: Epigenetic Changes Induced by Curcumin and other Natural Compounds. Genes Nutrition May 2011; 6(2) 93-108.
Nabel C, Kohli R: Demystifying DNA Demethylation. Science September 2011; 333(6047):1229-1230.
Vogel G: Do Jumping Genes Spawn Diversity? Science April, 2011; 332(6027):300-301.

What is claimed is:

1. A multi-component pharmaceutical composition consisting of:
about 0.01% to about 5% by weight methylsulfonylmethane,
about 5% to about 99% by weight of fructose 1,6-diphosphate, and
about 0.01% to about 95% by weight of one nutritional component selected from the group consisting of docosahexaenoic acid, resveratrol, and blueberry.

2. The multi-component pharmaceutical composition as recited in claim 1, wherein said one nutritional component consists of resveratrol, and said composition comprises about 85% to about 95% by weight of resveratrol.

3. The multi-component pharmaceutical composition as recited in claim 2, comprising about 5% to 15% by weight of fructose 1,6-diphosphate.

4. A method of treating or preventing neurodegenerative disease comprising administering to a subject having neurodegenerative disease an effective amount of the multi-component composition of claim 1.

5. A method of treating or preventing cognitive decline comprising administering to a subject having cognitive decline an effective amount of the multi-component composition as recited in claim 1.

* * * * *